(12) United States Patent
Kinsho et al.

(10) Patent No.: US 7,122,250 B2
(45) Date of Patent: Oct. 17, 2006

(54) COMPOSITE RESIN PARTICLE WITH SPECIFIC SHAPE FACTOR

(75) Inventors: Toshihiko Kinsho, Uji (JP); Hidetoshi Noda, Otsu (JP); Kazuyuki Hirai, Kusatsu (JP)

(73) Assignee: Sanyo Chemical Industries, Inc., Kyoto-Fu (JP)

( * ) Notice: Subject to any disclaimer, the term of this patent is extended or adjusted under 35 U.S.C. 154(b) by 0 days.

(21) Appl. No.: 10/836,830

(22) Filed: Apr. 30, 2004

(65) Prior Publication Data

US 2005/0031871 A1    Feb. 10, 2005

Related U.S. Application Data

(63) Continuation-in-part of application No. PCT/JP02/11390, filed on Oct. 31, 2002.

(30) Foreign Application Priority Data

Nov. 2, 2001 (JP) ............................. 2001-338794
Nov. 2, 2001 (JP) ............................. 2001-338800

(51) Int. Cl.
*B32B 5/16* (2006.01)

(52) U.S. Cl. ................................... 428/407

(58) Field of Classification Search ................ 428/407
See application file for complete search history.

(56) References Cited

U.S. PATENT DOCUMENTS

| 4,837,107 | A |   | 6/1989 | Axelsson et al. |
| 5,863,697 | A |   | 1/1999 | Uchiyama et al. |
| 6,106,990 | A | * | 8/2000 | Tazawa et al. ......... 430/137.19 |
| 2003/0125479 | A1 |   | 7/2003 | Kinsho et al. |

FOREIGN PATENT DOCUMENTS

| EP | 1 283 236 A1 | 2/2003 |
| WO | WO-01/60893 A | 8/2001 |

* cited by examiner

*Primary Examiner*—H. Thi Le
(74) *Attorney, Agent, or Firm*—Edwards Angell Palmer & Dodge LLP; John B. Alexander

(57) ABSTRACT

The invention is a composite resin particle useful as an additive for paints or coatings, powder coatings, cosmetic additives, slush molding resins, spacer for electronic part assembly, standard particles for electric measurement devices, toner, hot melt adhesive as well as other molding materials. Said composite resin particle comprises a resin microparticle (A) depositing on the surface of a resin particle (B) wherein the shape factor (SF-1) of said composite resin particle is 115 to 800. It is also a composite resin particle comprising a resin microparticle (A) depositing on the surface of a resin particle (B) wherein the acid vale of a resin (b) constituting the resin particle (B) is 5 to 100.

20 Claims, No Drawings

COMPOSITE RESIN PARTICLE WITH SPECIFIC SHAPE FACTOR

This application is a continuation-in-part of International Application PCT/JP02/11390, with an international filing date of Oct. 31, 2002, now abandoned.

FIELD OF THE INVENTION

The present invention relates to a composite resin particle. More particularly, the invention relates to a composite resin particle useful as additives in paints or coatings, powder coatings, cosmetic additives, slush molding resins, spacer for electronic part assembly, electric measurement device standard particles, toner, hot melt adhesives as well as other molding materials.

BACKGROUND OF THE INVENTION

A resin particle produced by dispersing a resin solution prepared beforehand by dissolving a resin in a solvent in an aqueous solvent in the presence of a dispersing (auxiliary) agent such as a surfactant or a water-soluble polymer followed by removing the solvent by heating or under reduced pressure has been known (solubilized resin suspending method, see for example, Jpn. unexamined patent publication 9-34167).

However, a resin particle obtained by a solubilized resin suspending method suffers from a defect which is experienced as a reduced affinity, when being melted by heating, to a substrate such as a metal, paper or wood material. Accordingly, the resin particle described above, when used as a paint additive, exhibits a poor adhesiveness to a substrate which disadvantageously allows the paint to be peeled off easily, and also exhibits, when used as a toner, a poor adhesiveness to a paper which disadvantageously allows to off-set to occur easily upon fixing at a low temperature. In addition, the resin particle described above also allows the powder flawability to be elevated excessively, resulting in a disadvantageously deteriorated painting performance due to a reduced viscosity of the paint when employed as a paint additive.

One objective of the present invention is to provide a resin particle exhibiting a satisfactory adhesion (adhesiveness) to a substrate. Another objective of the present invention is to provide a resin particle whose powder flawability and viscosity profile are excellent.

SUMMARY OF THE INVENTION

The present inventor made an effort to achieve the objectives described above, and discovered that a composite particle resin having specific shape factor and/or specific acid value can solve the problems described above, whereby establishing the present invention.

Thus, the first aspect of the present invention is a composite resin particle comprising a resin microparticle (A) depositing on the surface of a resin particle (B) wherein the shape factor (SF-1) of said composite resin particle is 115 to 800.

The second aspect of the present invention is a composite resin particle comprising a resin microparticle (A) depositing on the surface of a resin particle (B) wherein the acid value of a resin (b) constituting the resin particle (B) is 5 to 100.

BEST MODE FOR CARRYING OUT THE INVENTION

In the present invention, the shape factor (SF-1) is a value obtained by sampling 100 images of a composite resin particle randomly which have been subjected to a 500-fold magnification using an electron microscope (for example, Hitachi, Ltd. model FE-SEM (S-800) and the like, hereinafter the same applies) followed by introducing the image data via an interface to an image analyzer [for example, nexus NEW CUBE ver. 2.5 (NEXUS) and LuzexIII (NICORE CORPORATION) and the like, hereinafter the same applies] by which the analysis is conducted for a calculation in accordance with the equation (1) shown below.

$$(SF\text{-}1) = 100 \, \pi L^2 / 4S \quad (1)$$

wherein L is the absolute maximum length of the composite resin particle, S is a projected area of the composite resin particle.

In the first aspect of the present invention, the shape factor (SF-1) is a measure of the flatness of a composite resin particle, and is usually 115 to 800. The upper limit is preferably 500, more preferably 300, while the lower limit is preferably 120, more preferably 130, especially 135, most preferably 145. When using as the resin (b) constituting the resin particle (B) one whose acid value is 5 to 100 (the second aspect of the invention), the lower limit may be less than 115 (for example 105).

Since a value of the (SF-1) within the range specified above readily provides a marked thixotropy upon dispersing in a solvent or in an aqueous solvent when using the composite resin particle as a paint or coating additive, a suitability especially as a fluidity improving agent for a paint or a coating is exhibited. In addition, it also allows the composite resin particles to be aligned in the longitudinal direction upon forming a coating film, resulting in an advantage such as a suppression of swelling or a promotion of luster or gloss.

For the use as an additive for a paint or coating, the (SF-1) is preferably 115 to 800. The lower limit is more preferably 120, especially 130, most preferably 135, in particular 145. The upper limit is more preferably 500, especially 300.

A particle having a value of the (SF-1) within the range specified above allows a smooth touch to be experienced upon application to a skin when incorporated into a cosmetic product (lipstick, foundation and the like). When using as a slush molding resin or a hot melt adhesive, a powder fluidity and a powder cut off can readily be improved.

When using as a cosmetic additive, slush molding resin or hot melt adhesive, the value of the (SF-1) is preferably 115 to 500. The upper limit is more preferably 300, especially 200. The lower limit is more preferably 120, especially 130, most preferably 135, in particular 145.

A particle having a value of the (SF-1) within the range specified above gives an improved cleaning performance at a cleaning blade when used as a toner for an electrophotography, electrostatic recording and electrostatic printing.

For the use as a toner, the (SF-1) is preferably 115 to 400. The upper limit is more preferably 300, especially 250. The lower limit is more preferably 120, especially 130, most preferably 135, in particular 145.

While the shape factor (SF-1) represents a degree of the flatness of a composite resin particle, another shape factor (SF-2) representing a degree of the irregularity of the surface of a composite resin particle is also useful.

A shape factor (SF-2) is a value obtained by sampling 50 images of a composite resin particle randomly which have been subjected to a 3500-fold magnification using an electron microscope followed by introducing the image data via an interface to an image analyzer by which the analysis is conducted for a calculation in accordance with the equation (2) shown below.

$$(SF\text{-}2)=100\,\pi P^2/4S \qquad (2)$$

wherein P is a circumferential length of the composite resin particle, S is a projected area of the composite resin particle.

The shape factor (SF-2) of the composite resin particle according to the invention is preferably 100 to 500. Within this range, the following advantageous effects can be obtained depending on the applications of the composite resin.

For example, when using a composite resin particle as a paint or coating additive, it can readily be dispersed in a solvent or an aqueous solvent in view of the viscosity.

For the use as a paint or coating additive, the (SF-2) is more preferably 140 to 500, especially 150 to 500.

The use as a cosmetic additive (lipstick, foundation and the like), a slush molding resin or a hot melt adhesive gives a satisfactory applying and painting performance.

For the use as a cosmetic additive, a slush molding resin or a hot melt adhesive, the (SF-2) is more preferably 100 to 300, especially 100 to 250.

The use as a toner for electrophotography, electrostatic recording and electrostatic printing gives satisfactory cleaning performance at a cleaning blade and off-set performance.

For the use as a toner, the upper limit of the (SF-2) is more preferably 400, especially 300, while the lower limit is more preferably 110, especially 115.

The particle diameter of the resin microparticle (A) is smaller that the particle diameter of the resin particle (B), and in view of the particle diameter uniformity, the ratio (DA/DB) of the volume average particle diameter (DA) of the resin microparticle (A) to the volume average particle diameter (DB) of the resin particle (B) is preferably 0.0001 to 0.5. The upper limit is more preferably 0.4, especially 0.3, while the lower limit is more preferably 0.0005, especially 0.001. Within this range, the particle (A) can more readily be adsorbed on the surface of the particle (B), resulting in a more sharp particle size distribution of the composite resin particle.

The volume average particle diameter (DA) is preferably 0.0005 to 30 µm. The upper limit of the (DA) is more preferably 20 µm, especially 10 µm, while the lower limit is more preferably 0.01 µm, especially 0.02 µm, particularly 0.04 µm. Within this range, the (SF-1) of the composite resin particle can readily be within the preferable range.

The volume average particle diameter (DB) is preferably 0.1 to 300 µm. The upper limit of the (DB) is more preferably 250 µm, especially 200 µm, while the lower limit is more preferably 0.5 µm, especially 1 µm. Within this range, the (SF-1) of the composite resin particle can readily be within the preferable range.

A volume average particle diameter can be measured for example by a laser particle size distribution meter (for example, trade name: LA-920 (HORIBA, Ltd.), or trade name: MULTITIZER III (Coulter)).

The amount of the resin microparticle (A) based on the total weight of the resin microparticle (A) and the resin particle (B) in the composite resin particle is preferably 0.01 to 60% by weight (hereinafter a % means a % by weight unless otherwise specified) in view of a higher uniformity of the particle diameter and a storage stability of the composite resin particle. The upper limit of the amount of the resin microparticle (A) is more preferably 55%, especially 50%, while the lower limit is more preferably 0.05%, especially 0.1%.

The ratio (TA/TC) of the projected area (TA) of the resin microparticle (A) to the projected area (TC) of the composite resin particle is preferably 0.001 to 1, more preferably 0.002 to 1, especially 0.005 to 1. Within this range, the particle fluidity, storage stability, dispersion stability in an aqueous solvent and other solvents of the composite particle can readily be improved.

The projected area can be determined by shooting the electron microscope photograph of the surface of a sample (magnification: 30,000 times) ten times followed by introducing the image data of each surface image via an interface into an image analyzer.

The volume average particle diameter (DC) of the composite resin particle is preferably 0.2 to 400 µm. The upper limit of the (DC) is more preferably 300 µmm especially 250 µm, while the lower limit is more preferably 0.8 µm, especially 1 µm. Within this range, the handling of the composite resin particle can further be improved.

The variation coefficient of the volume average particle diameter (DC) of the composite resin particle is preferably 0.1 to 50% in view of the particle diameter uniformity of the composite resin particle, more preferably 0.1 to 30%, especially 0.1 to 15%. Within this range, the particle diameter becomes uniform, and the performances including fluidity, electric and charging characteristics and heat melting characteristics can readily be uniform.

The variation coefficient can be calculated by the equation (3) shown below.

$$\text{Variation coefficient (\%)}=100\times\{\text{Standard deviation of }(DC)\}/(DC) \qquad (3)$$

The ratio (DC/DNC) of the volume average particle diameter (DC) of the composite resin particle to the number average particle diameter (DNC) of the composite resin is preferably 1.0 to 2.5 in view of the particle diameter uniformity of the composite resin particle, more preferably 1.0 to 1.3, especially 1.0 to 1.2.

A number average particle diameter can be determined for example by a Coulter counter (for example, trade name: MULTITIZER III (Coulter)).

The composite resin particle preferably has a resin particle (B) with no outer shell layer formed by filming of a resin.

The resin microparticle (A) comprises a resin (a).

The resin (a) may for example be either a thermoplastic resin or a thermosetting resin, including vinyl resins, polyurethanes, epoxy resins, polyesters, polyamides, polyimides, silicone resins, phenol resins, melamine resins, urea resin, aniline resins, ionomer resins, polycarbonates as well as mixtures thereof. Among those listed above, those preferred because of the readiness of obtaining a uniform microspheric resin microparticle are vinyl resins, polyurethanes, epoxy resins, polyesters and mixtures thereof, with vinyl resins, polyurethanes, polyesters and mixture thereof being more preferred and vinyl resins, polyesters and mixtures thereof being especially preferred.

Among those of the resin (a) listed above, the preferred resins, i.e., vinyl resins, polyurethanes, epoxy resins and polyesters are further discussed below, although other resins can similarly be employed.

A vinyl resin is a polymer obtained by homopolymerizing or copolymerizing a vinyl monomer.

A polymerization can employ a known polymerization catalyst.

As the vinyl monomer, any of the following (1) to (10) can be employed.

(1) Vinylic Hydrocarbons:

(1-1) Aliphatic vinylic hydrocarbons: An alkene having 2 to 12 carbon atoms (ethylene, propylene, butene, isobutylene, pentene, heptene, diisobutylene, octene, dodecene, octadecene and α-olefin having 3 to 24 carbon atoms and the like); alkadiene having 4 to 12 carbon atoms (butadiene, isoprene, 1,4-pentadiene, 1,6-hexadiene and 1,7-octadiene and the like).

(1-2) Alicyclic vinylic hydrocarbons: A mono- or di-cycloalkene having 6 to 15 carbon atoms (cyclohexene, vinylcyclohexene and ethylidene bicycloheptene and the like), mono- or di-cycloalkadiene having 5 to 12 carbon atoms ((di)cyclopentadiene and the like); and terpene (limonene, indene and the like).

(1-3) Aromatic vinylic hydrocarbons: styrene; hydrocarbyl (alkyl, cycloalkyl, aralkyl and/or alkenyl having 1 to 24 carbon atoms)-substituted styrene (α-methylstyrene, vinyltoluene, 2,4-dimethylstyrene, ethylstyrene, isopropylstyrene, butylstyrene, phenylstyrene, cyclohexylstyrene, benzylstyrene, crotylbenzene, divinylbenzene, divinyltoluene, divinylxylene and trivinylbenzene); and vinylnaphthalene and the like.

(2) Carboxyl Group-containing Vinyl Monomers and Their Salts:

An unsaturated monocarboxylic acid having 3 to 30 carbon atoms ((meth)acrylic acid (including to acrylic acid and/or methacrylic acid, hereinafter the same applies), crotonic acid, isocrotonic acid, cinnamic acid and the like); unsaturated dicarboxylic acid (anhydride) having 3 to 30 carbon atoms ((anhydrous) maleic acid, fumaric acid, itaconic acid, (anhydrous) citraconic acid, mesaconic acid and the like); and monoalkyl (1 to 24 carbon atoms) ester of unsaturated dicarboxylic acid having 3 to 30 carbon atoms (monomethyl maleate, monooctadecyl maleate, monoethyl fumarate, monobutyl itaconate, itaconic acid glycol monoether, monoeicosyl citraconate and the like) and the like.

A carboxyl group-containing vinyl monomer salt may for example be an alkaline metal salt (sodium salt, potassium salt and the like), alkaline earth metal salt (calcium salt, magnesium salt and the like), ammonium salt, amine salt or quaternary ammonium salt. While the amine salt may be any amine compound, those which may be exemplified are primary amine salts (ethylamine salts, butylamine salts, octylamine salts and the like), secondary amines (diethylamine salts, dibutylamine salts and the like), tertiary amines (triethylamine salts, tributylamine salts and the like). A quaternary amine salt may for example be a tetraethylammonium salt, triethyllaurylammonium salt, tetrabutylammonium salt, tributyllaurylammonium salt and the like.

A carboxyl group-containing vinyl monomer salt may for example be sodium acrylate, sodium methacrylate, monosodium maleate, disodium maleate, potassium acrylate, potassium methacrylate, monopotassium maleate, lithium acrylate, cesium acrylate, ammonium acrylate, calcium acrylate and aluminum acrylate.

(3) Sulfo Group-containing Vinyl Monomers and Their Salts:

An alkenesulfonic acid having 2 to 14 carbon atoms (vinylsulfonic acid (meth)allylsulfonic acid, methylvinylsulfonic acid and the like); styrenesulfonic acid and its alkyl (2 to 24 carbon atoms) derivative (α-methylstyrenesulfonic acid and the like);

sulfo(hydroxy)alkyl-(meth)acrylate having 5 to 18 carbon atoms (sulfopropyl (meth)acrylate, 2-hydroxy-3-(meth)acryloxypropylsulfonic acid, 2-(meth)acryloyloxyethanesulfonic acid, 3-(meth)acryloyloxy-2-hydroxypropanesulfonic acid and the like);

sulfo(hydroxy)alkyl(meth)acrylamide having 5 to 18 carbon atoms (2-(meth)acryloylamino-2,2-dimethylethanesulfonic acid, 2-(meth)acrylamide-2-methylpropanesulfonic acid, 3-(meth)acrylamide-2-hydroxypropanesulfonic acid); alkyl (3 to 18 carbon atoms) allylsulfosuccinic acid (propylallylsulfosuccinic acid, butylallylsulfosuccinic acid, 2-ethylhexyl-allylsulfosuccinic acid); poly [n (polymerization degree, hereinafter the same applies)=2 to 30] oxyalkylene(oxyethylene, oxypropylene, oxybutylene: homo, random or block) mono(meth)acrylate sulfuric acid ester [poly (n=5 to 15) oxyethylene monomethacrylate sulfuric acid ester, poly (n=5 to 15) oxypropylene monomethacrylate sulfuric acid ester and the like];

compounds represented by general formulae (1-1) to (1-3) as well as the salts thereof.

A salt may employ a counterion indicated for (2) a carboxyl group-containing vinyl monomer and its salt.

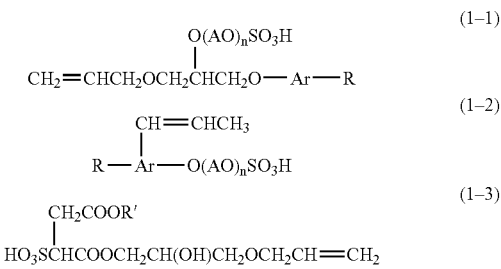

wherein R is an alkyl group of 1 to 15 carbon atoms, A is an oxyalkylene group of 2 to 4 carbon atoms and may be same or different when n is two or more, and may be random, block and/or mixture thereof when different; Ar is a benzene ring, n is an integer of 1 to 50, R' is an alkyl group of 1 to 15 carbon atoms which may be substituted by a fluorine atom.

(4) Phosphono Group-containing Vinyl Monomers and Their Salts:

A (meth)acryloyloxyalkyl monophosphate (alkyl group having 1 to 24 carbon atoms) (2-hydroxyethyl(meth)acryloyl phosphate, phenyl-2-acryloyloxyethyl phosphate and the like), (meth)acryloyloxyalkyl phosphonic acid (alkyl group having 1 to 24 carbon atoms) (2-acryloyloxyethylphosphonic acid and the like).

(5) Hydroxyl Group-containing Vinyl Monomers:

Hydroxystyrene, N-methylol(meth)acrylamide, hydroxyethyl (meth)acrylate, hydroxypropyl (meth)acrylate, polyethylene glycol mono(meth)acrylate, (meth)allyl alcohol, crotyl alcohol, isocrotyl alcohol, 1-butene-3-ol, 2-butene-1-ol, 2-butene-1,4-diol, propargyl alcohol, 2-hydroxyethylpropenyl ether, sucrose allyl ether and the like.

(6) Nitrogen-containing Vinyl Monomers:

(6-1) Amino Group-containing Vinyl Monomers:

Aminoethyl (meth)acrylate, dimethylaminoethyl (meth)acrylate, diethylaminoethyl (meth)acrylate, t-butylaminoethyl methacrylate, N-aminoethyl (meth)acrylamide, (meth)allylamine, morpholinoethyl (meth)acrylate, 4-vinylpyridine, 2-vinylpyridine, crotylamine, N,N-dimethylaminostyrene, methyl α-acetoaminoacrylate, vinylimidazole, N-vinylpyrrole, N-vinylthiopyrrolidone, N-aryl phenylene diamine, aminocarbazole, aminothiazole, aminoindole, aminopyrrole, aminoimidazole, aminomercaptothiazole, salts thereof and the like.

(6-2) Amide Group-containing Vinyl Monomers:

(Meth)acrylamide, N-methyl (meth)acrylamide, N-butyl acrylamide, diacetone acrylamide, N-methylol (meth)acrylamide, N,N'-methylenebis(meth)acrylamide, cinnamyl amide, N,N-dimethyl acrylamide, N,N-dibenzyl acrylamide, methacryl formamide, N-methyl N-vinylacetamide, N-vinylpyrrolidone and the like.

(6-3) Nitrile Group-containing Vinyl Monomers of 3 to 10 Carbon Atoms:

(Meth)acrylonitrile, cyanostyrene and cyanoacrylate and the like.

(6-4) Quaternary Ammonium Cation-carrying Group-containing Vinyl Monomers:

A quaternized derivative of a tertiary amino group-containing vinyl monomer such as dimethylaminoethyl (meth)acrylate, diethylaminoethyl (meth)acrylate, dimethylaminoethyl (meth)acrylamide, diethylaminoethyl (meth)acrylamide and the like (quaternized using a quaternizing agent such as methyl chloride, dimethylsulfuric acid, benzyl chloride, dimethyl carbonate and the like, for example, dimethylammonium chloride, trimethylallylammonium chloride and the like).

(6-5) Nitro Group-containing Vinyl Monomers of 8 to 12 Carbon Atoms: Nitrostyrene and the like.

(7) Epoxy Group-containing Vinyl Monomers of 6 to 18 Carbon Atoms:

Glycidyl (meth)acrylate, tetrahydrofuryl (meth)acrylate, p-vinylphenyloxide and the like.

(8) Halogen-containing Vinyl Monomers of 2 to 16 Carbon Atoms:

Vinyl chloride, vinyl bromide, vinylidene chloride, acryl chloride, chlorostyrne, bromostyrene, dichlorostyrene, chloromethylstyrene, tetrafluorostyrene, chloroprene and the like.

(9) Vinyl Esters, Vinyl (Thio)ether, Vinyl Ketones, Vinylsulfones:

(9-1) Vinyl Esters of 4 to 16 Carbon Atoms:

For example, vinyl acetate, vinyl propionate, vinyl butyrate, diallyl phthalate, diallyl adipate, isopropenyl acetate, vinyl methacrylate, methyl 4-vinyl benzoate, cyclohexyl methacrylate, benzyl methacrylate, phenyl (meth)acrylate, vinyl methoxyacetate, vinyl benzoate, ethyl α-ethoxyacrylate, alkyl (meth)acrylate having an alkyl group of 1 to 50 carbon atoms [methyl (meth)acrylate, ethyl (meth)acrylate, propyl (meth)acrylate, butyl (meth)acrylate, 2-ethylhexyl (meth)acrylate, dodecyl (meth)acrylate, hexadecyl (meth)acrylate, heptadecyl (meth)acrylate, eicosyl (meth)acrylate and the like], dialkyl fumarate (each of the two alkyl groups is a straight, branched or alicyclic group of 2 to 8 carbon atoms), dialkyl maleate (each of the two alkyl groups is a straight, branched or alicyclic group of 2 to 8 carbon atoms), poly (meth)allyloxyalkanes [diallyloxyethane, triallyloxyethane, tetraallyloxyethane, tetraallyloxypropane, tetraallyloxybutane, tetramethallyloxyethane and the like], polyalkylene glycol chain-containing vinylic monomer [polyethylene glycol (molecular weight: 300) mono(meth)acrylate, polypropylene glycol (molecular weight: 500) monoacrylate, methylalcohol ethylene oxide (hereinafter abbreviated as EO) 10-mole adduct (meth)acrylate, lauryl alcohol EO 30-mole adduct (meth)acrylate and the like], poly (meth)acrylates [polyhydric alcohol (meth)acrylate: ethylene glycol di(meth)acrylate, propylene glycol di(meth)acrylate, neopentyl glycol di(meth)acrylate, trimethylolpropane tri(meth)acrylate, polyethylene glycol di(meth)acrylate and the like] and the like.

(9-2) Vinyl Thioethers of 3 to 16 Carbon Atom:

For example, vinylmethyl ether, vinylethyl ether, vinylpropyl ether, vinylbutyl ether, vinyl 2-ethylhexyl ether, vinylphenyl ether, vinyl 2-methoxyethyl ether, methoxybutadiene, vinyl 2-butoxyethyl ether, 3,4-dihydro-1,2-pyrane, 2-butoxy-2'-vinyloxydiethyl ether, vinyl 2-ethylmercaptoethyl ether, acetoxystyrene, phenoxystyrene.

(9-3) Vinyl Ketone of 4 to 12 Carbon Atoms (Vinyl Methyl Ketone, Vinyl Ethyl Ketone, Vinyl Phenyl Ketone and the Like):

A vinyl sulfone of 2 to 16 carbon atoms (divinyl sulfide, p-vinyldiphenyl sulfide, vinylethyl sulfide, vinylethylsulfone, divinylsulfone, divinyl sulfoxide and the like) and the like.

(10) Other Vinyl Monomers:

Isocyanatoethyl (meth)acrylate, m-isopropenyl-α, α-dimethylbenzyl isocyanate and the like.

Among the vinyl monomers listed above, vinyl hydrocarbons, carboxyl group-containing vinyl monomers and their salts, sulfonate group-containing vinyl monomers and their salts, hydroxyl group-containing vinyl monomers and nitrogen-containing vinyl monomers are preferred, and those more preferred are vinyl hydrocarbons, carboxyl group-containing vinyl monomers and their salts, sulfonate group-containing vinyl monomer and their salts, and those preferred especially are aromatic vinylic hydrocarbons, carboxyl group-containing vinyl monomers and their salts and sulfonate group-containing vinyl monomer and their salts.

Among vinyl resins, the polymer obtained by copolymerizing vinyl monomers (vinyl monomer copolymer) is a polymer obtained by a binary or higher copolymerization of any combination of the monomers (1) to (10) described above at any ratio, including styrene-(meth)acrylate copolymers, styrene-butadiene copolymers, (meth)acrylic acid-(meth)acrylate copolymers, styrene-acrylonitrile copolymers, styrene-(anhydrous) maleic acid copolymers, styrene-(meth)acrylic acid copolymers, styrene-(meth)acrylic acid-divinylbenzene copolymers and styrene-styrenesulfonic acid-(meth)acrylate copolymer.

Since the composite resin particle of the present invention is obtained preferably by means of a production method comprising a step for dispersing the resin (b), a precursor (b0) of said resin (b) or a solution thereof in an aqueous dispersion containing a resin microparticle (A), it is preferred to disperse the resin microparticle (A) in an aqueous dispersion. Accordingly, it is preferred that the resin (a) is not completely dissolved in water at least under a condition allowing an aqueous dispersion to be formed (usually 5 to 90° C.). As a result, when a vinyl resin is a copolymer, the ratio of a hydrophobic monomer and a hydrophilic monomer constituting in the vinyl resin may vary depending on the types of the monomers selected but usually the amount of the hydrophobic monomer is preferably 10% or more based on the total weight of the monomers, more preferably 30% or more. An amount of the hydrophobic monomer of 10% or less may allow the vinyl resin to be water-soluble, resulting in a tendency to lose the particle diameter uniformity of the composite resin particle.

As used herein, a hydrophilic monomer means a monomer 100 g or more of which can be dissolved in 100 g of water at 25° C., while a hydrophobic monomer means any of other monomers (a monomer 100 g or more of which can not be dissolved in 100 g of water at 25° C.) (the same applies to resins mentioned hereinafter).

A polyester may be a polycondensates of a polyol with a polycarboxylic acid, its anhydride or its lower alkyl (alkyl group having 1 to 4 carbon atoms) ester and the like.

A polycondensation reaction can employ a known polycondensation catalyst.

The polyol is a diol (11) and a 3- to 8- or higher valent polyol (12).

The polycarboxylic acid, its anhydride or its lower alkyl ester may for example be a dicarboxylic acid (13), a 3- to 6- or higher valent polycarboxylic acid (14), its acid anhydride and its lower alkyl ester.

The diol (11) may for example be an alkylene glycol of 2 to 30 carbon atoms (ethylene glycol, 1,2-propylene glycol, 1,3-propylene glycol, 1,4-butanediol, 1,6-hexanediol, octanediol, decanediol, dodecanediol, tetradecanediol, neopentyl glycol, 2,2-diethyl-1,3-propanediol and the like); alkylene ether glycol having a molecular weight of 106 to 10000 (diethylene glycol, triethylene glycol, dipropylene glycol, polyethylene glycol, polypropylene glycol, polytetramethylene ether glycol and the like); alicyclic diol of 6 to 24 carbon atoms (1,4-cyclohexane dimethanol, hydrogenated bisphenol A and the like); bisphenol of 15 to 30 carbon atoms (bisphenol A, bisphenol F, bisphenol S and the like); and polyphenol of 12 to 24 carbon atoms (cathecol, hydroquinone, resorcin and the like); alkylene oxide (EO, propylene oxide (hereinafter abbreviated as PO), butylene oxide and the like) adduct (added molar number: 2 to 100) of an above-mentioned alicyclic diol having a molecular weight of 100 to 10000 (10-mole EO adduct of 1,4-cyclohexane dimethanol and the like); alkylene oxide (EO, PO, butylene oxide and the like) adduct (added molar number: 2 to 100) of an above-mentioned bisphenol (bisphenol A 2- to 4-mole EO adduct, bisphenol A 2- to 4-mole PO adduct and the like); polylactonediol having a weight average molecular weight of 100 to 50000 (poly ε-caprolactonediol and the like); polybutadienediol having a weight average molecular weight of 1000 to 20000 and the like.

Among those listed above, an alkylene glycol and a bisphenol alkylene oxide adduct are preferable, and those more preferred are a bisphenol alkylene oxide adduct and a mixture thereof with an alkylene glycol.

The 3- to 8- or higher valent polyol (12) may for example be a 3- to 8- or higher valent aliphatic polyhydric alcohol of 3 to 8 carbon atoms (glycerin, trimethyrolethane, trimethylolpropane, pentaerythritol, sorbitan, sorbitol and the like); trisphenol of 25 to 50 carbon atoms (trisphenol PA and the like); novolak resin having a polymerization degree of 3 to 50 (phenol novolak, cresol novolak and the like); polyphenol of 6 to 30 carbon atoms (pyrogallol, fluoroglucinol, 1,2,4-benzenetriol and the like); above-mentioned trisphenol alkylene (2 to 4 carbon atoms) oxide adduct (added molar number: 2 to 100) (for example, trisphenol PA 2- to 4-mole EO adduct, trisphenol PA 2- to 4-mole PO adduct and the like); above-mentioned novolak resin alkylene (2 to 4 carbon atoms) oxide adduct (added molar number: 2 to 100) (phenol novolak 2-mole PO adduct, phenol novolak 4-mole EO adduct and the like); above-mentioned polyphenol alkylene (2 to 4 carbon atoms) oxide adduct (added molar number: 2 to 100) (pyrogallol 4-mole EO adduct); and acrylpolyol having a polymerization degree of 20 to 2000 [copolymer of hydroxyethyl (meth)acrylate with other vinyl monomer (for example, styrene, (meth)acrylic acid, (meth) acrylate and the like)] and the like.

Among those listed above, an aliphatic polyhydric alcohol and a novolak resin alkylene oxide adduct are preferred, with a novolak resin alkylene oxide adducts being more preferred.

The dicarboxylic acid (13) may for example be an alkane dicarboxylic acid of 4 to 32 carbon atoms (succinic acid, adipic acid, sebacic acid, azelaic acid, sebacic acid, dodecanedicarboxylic acid, octadecane dicarboxylic acid and the like); alkenedicarboxylic acid of 4 to 32 carbon atoms (maleic acid, fumaric acid, citraconic acid, mesaconic acid and the like); branched alkenedicarboxylic acid of 8 to 40 carbon atoms [dimeric acid, alkenylsuccinic acid (dodecenylsuccinic acid, pentadecenylsuccinic acid, octadecenylsuccinic acid and the like); branched alkanedicarboxylic acid of 12 to 40 carbon atoms [alkylsuccinic acid (decylsuccinic acid, dodecylsuccinic acid, octadecylsuccinic acid and the like); aromatic dicarboxylic acid of 8 to 20 carbon atoms (phthalic acid, isophthalic acid, terephthalic acid, naphthalenedicarboxylic acid and the like) and the like.

Among those listed above, an alkenedicarboxylic acid and an aromatic dicarboxylic acid are preferred, with an aromatic dicarboxylic acid being more preferred.

The 3- to 4- or higher valent polycarboxylic acid (14) may for example be an aromatic polycarboxylic acid of 9 to 20 carbon atoms (trimellitic acid, pyromellitic acid and the like).

The acid anhydride of a dicarboxylic acid (13) or the 3- to 4- or higher valent polycarboxylic acid (14) may for example be trimellitic anhydride, pyromellitic anhydride and the like. Its lower alkyl ester may for example be a methyl ester, ethyl ester, isopropyl ester and the like.

The polyester may for example be a diol, 3- to 6- or higher valent polyol, dicarboxylic acid, 3- to 4- or higher valent polycarboxylic acid and mixtures thereof, which may be employed at any ratio. The equivalence ratio [OH]/[COOH] of the hydroxyl group [OH] and the carboxyl group [COOH] is preferably 2/1 to 1/1, more preferably 1.5/1 to 1/1, especially 1.3/1 to 1.02/1.

The ester group equivalent (molecular weight per ester group) in a polyester is preferably 103 to 2000. The upper limit is more preferably 1000, especially 500, while the lower limit is more preferably 120, especially 140.

The polyurethane may for example be a polyadduct of the polyisocyanate (15) and an active hydrogen-carrying compound (β1) {water, diol (11), 3- to 6- or higher valent polyol (12), dicarboxylic acid (13), 3- to 4- or higher valent polycarboxylic acid (14), polyamine (16), polythiol (17) and the like}.

A polyaddition reaction can employ a known polyaddition reaction catalyst.

The polyisocyanate (15) may for example be an aromatic polyisocyanate of 6 to 20 carbon atoms (excluding the carbon atoms in an NCO group, hereinafter the same applies), aliphatic polyisocyanate of 2 to 18 carbon atoms, alicyclic polyisocyanate of 4 to 15 carbon atoms, araliphatic polyisocyanate of 8 to 15 carbon atoms as well as a modified compound of such a polyisocyanate (modified compound containing an urethane, group, carbodiimide group, allophanate group, urea group, biuret group, urethodione group, urethoimine group, isocyanurate group, oxazolidone group and the like) and mixtures of any two ore more substances listed above.

The aromatic polyisocyanate may for example be 1,3- or 1,4-phenylene diisocyanate, 2,4- or 2,6-tolylene diisocyanate (TDI), crude TDI, 2,4'- or 4,4'-diphenylmethane diisocyanate (MDI), crude MDI [crude diaminophenylmethane <condensates of formaldehyde and an aromatic amine (aniline) or its mixture; mixture of diaminodiphenylmethane and a small amount (for example 5 to 20%) of a trifunctional or hither polyamine> derivatized with phosgene; polyallyl polyisocyanate (PAPI)], 1,5-naphthylene diisocyanate, 4,4', 4"-triphenylmethane triisocyanate, m- or p-isocyanatopenyl-sulfonyl isocyanate and mixtures thereof.

The aliphatic polyisocyanate may for example be ethylene diisocyanate, tetramethylene diisocyanate, hexamethylene diisocyanate (HDI), dodecamethylene diisocyanate, 1,6,11-undecane triisocyanate, 2,2,4-trimethylhexamethylene diisocyanate, lysine diisocyanate, 2,6-diisocyanatomethyl-caproate, bis(2-isocyanatoethyl)fumarate, bis(2-isocyanato-ethyl)carbonate, 2-isocyanatoethyl-2,6-diisocyanatohex-anoate and mixtures thereof.

The alicyclic polyisocyanate may for example be isophor-one dilsocyanate (IPDI), dicyclohexylmethane-4,4'-diisocy-anate (hydrogenated MDI), cyclohexylene diisocyanate, methylcyclohexylene diisocyanate (hydrogenated TDI), bis (2-isocyanatoethyl)-4-cyclohexene-1,2-dicarboxylate, 2,5- or 2,6-norbornane diisocyanate as well as mixtures thereof.

The araliphatic polyisocyanate may for example be m- or p-xylylene diisocyanate (XDI), α,α,α',α'-tetramethylxy-lylene diisocyanate (TMXDI) as well as mixture thereof.

The modified polyisocyanate employed is a modified substance containing an urethane group, carbodiimide group, allophanate group, urea group, biuret group, urethodione group, urethoimine group, isocyanurate group and/or oxazolidone group, for example, such as a modified MDI (urethane-modified MDI, carbodiimide-modified MDI and trihydrocarbyl phosphate-modified MDI and the like), urethane-modified TDI and mixtures thereof [a mixture of a modified MDI and an urethane-modified TDI (isocyanate-containing prepolymer)] and the like.

Among those listed above, the aromatic polyisocyanate, aliphatic polyisocyanate and alicyclic polyisocyanate are preferred, with TDI, MDI, HDI, hydrogenated MDI and IPDI being more preferred.

The polyamine (16) has 2 to 8 or more of primary or secondary amino groups, including an aliphatic polyamine of 2 to 18 carbon atoms and an aromatic polyamine (6 to 20 carbon atoms) and the like.

An aliphatic polyamine of 2 to 18 carbon atoms may for example be [1] an aliphatic polyamine, [2] its alkyl (1 to 4 carbon atoms) or hydroxyalkyl (2 to 4 carbon atoms)-substituted form, [3] an alicyclic or heterocyclic ring-containing aliphatic polyamine and [4] an aromatic ring-containing aliphatic amine (8 to 15 carbon atoms) and the like.

[1] The aliphatic polyamine may for example be an alkylene diamine of 2 to 12 carbon atoms (ethylene diamine, propylene diamine, trimethylene diamine, tetramethylene diamine, hexamethylene diamine and the like) and a polyalkylene (2 to 6 carbon atoms) polyamine [diethylene triamine, iminobispropylamine, bis(hexamethylene)triamine, triethylene tetramine, tetraethylene pentamine, pentaethyl-ene hexamine and the like] and the like.

[2] Its alkyl (1 to 4 carbon atoms) or hydroxyalkyl (2 to 4 carbon atoms)-substituted form may for example be a dialkyl (1 to 3 carbon atoms) aminopropylamine, trimeth-ylhexamethylene diamine, aminoethyl ethanolamine, 2,5-dimethyl-2,5-hexamethylene diamine, methyliminobispro-pylamine and the like.

[3] The alicyclic or heterocyclic ring-containing aliphatic polyamine may for example be an alicyclic polyamine of 4 to 15 carbon atoms {1,3-diamunocyclohexane, isophorone diamine, menthene diamine, 4,4'-methylene dicyclohexane diamine (hydrogenated methylene dianiline), 3,9-bis(3-ami-nopropyl)-2,4,8,10-tetraoxaspiro[5,5]undecane and the like} and a heterocyclic polyamine of 4 to 15 carbon atoms {piperazine, N-aminoethylpiperazine, 1,4-diaminoethylpip-erazine, 1,4-bis(2-amino-2-methylpropyl)piperazine and the like} and the like.

[4] The aromatic ring-containing aliphatic amine (8 to 15 carbon atoms) may for example be xylylene diamine, tetra-chloro-p-xylylene diamine and the like.

The aromatic polyamine (6 to 20 carbon atoms) may be [1] an unsubstituted aromatic polyamine, [2] a nuclear-substituted alkyl group [an alkyl group of 1 to 4 carbon atoms such as methyl, ethyl, n- or i-propyl, butyl and the like]-carrying aromatic polyamine, [3] a nuclear-substituted electron-withdrawing group (halogen such as Cl, Br, I, F and the like); alkoxy group such as methoxy and ethoxy; nitro group and the like)-carrying aromatic polyamine, [4] a secondary amino group-carrying aromatic polyamine and the like.

[1] The unsubstituted aromatic polyamine may for example be 1,2-, 1,3- or 1,4-phenylene diamine, 2,4'-or 4,4'-diphenylmethane diamine, crude diphenylmethane diamine (polyphenylpolymethylene polyamine), diamino-diphenylsulfone, benzidine, thiodianiline, bis(3,4-diami-nophenyl)sulfone, 2,6-diaminopyridine, m-aminobenzy-lamine, triphenylmethane-4,4',4"-triamine, naphthylene diamine and mixtures thereof.

[2] The nuclear-substituted alkyl group (an alkyl group of 1 to 4 carbon atoms such as methyl, ethyl, n- or i-propyl, butyl and the like)-carrying aromatic polyamine may for example be 2,4- or 2,6-tolylene diamine, crude tolylene diamine, diethyltolylene diamine, 4,4'-diamino-3,3'-dimeth-yldiphenylmethane, 4,4'-bis(o-toluidine), dianisidine, diami-noditolyl sulfone, 1,3-dimethyl-2,4-diaminobenzene, 1,3-diethyl-2,4-diaminobenzene, 1,3-dimethyl-2,6-diaminobenzene, 1,4-diethyl-2,5-diaminobenzene, 1,4-diisopropyl-2,5-diaminobenzene, 1,4-dibutyl-2,5-diaminobenzene, 2,4-diaminomesitylene, 1,3,5-triethyl-2,4-diaminobenzene, 1,3,5-triisopropyl-2,4-diaminobenzene, 1-methyl-3,5-diethyl-2,4-diaminobenzene, 1-methyl-3,5-di-ethyl-2,6-diaminobenzene, 2,3-dimethyl-1,4-diaminonaph-thalene, 2,6-dimethyl-1,5-diaminonaphthalene, 2,6-diiso-propyl-1,5-diaminonaphthalene, 2,6-dibutyl-1,5-diaminonaphthalene, 3,3',5,5'-tetramethylbenzidine, 3,3',5, 5'-tetraisopropylbenzidine, 3,3',5,5'-tetramethyl-4,4'-diaminodiphenylmethane, 3,3',5,5'-tetraethyl-4,4'-diaminodiphenylmethane, 3,3',5,5'-tetraisopropyl-4,4'-diaminodiphenylmethane, 3,3',5,5'-tetrabutyl-4,4'-diaminodiphenylmethane, 3,5-diethyl-3'-methyl-2',4-diaminodiphenylmethane, 3,5-diisopropyl-3'-methyl-2',4-diaminodiphenylmethane, 3,3'-diethyl-2,2'-diaminodiphenylmethane, 4,4'-diamino-3,3'-dimethyldiphenylmethane, 3,3',5,5'-tetraethyl-4,4'-diaminobenzophenone, 3,3',5,5'-tetraisopropyl-4,4'-diaminobenzophenone, 3,3',5,5'-tetraethyl-4,4'-diaminodiphenyl ether, 3,3',5,5'-tetraisopropyl-4,4'-diaminodiphenyl sulfone and mixtures thereof.

[3] The nuclear-substituted electron-withdrawing group (halogen such as chlorine atom, bromine atom, iodine atom and fluorine atom; alkoxy group such as methoxy and ethoxy; nitro group)-carrying aromatic polyamine may for example be methylene bis-o-chloroaniline, 4-chloro-o-phenylene diamine, 2-chloro-1,4-phenylene diamine, 3-amino-4-chloroaniline, 4-bromo-1,3-phenylene diamine, 2,5-dichloro-1,4-phenylene diamine, 5-nitro-1,3-phenylene diamine, 3-dimethoxy-4-aminoaniline; 4,4'-diamino-3,3'-dimethyl-5,5'-dibromo-diphenylmethane, 3,3'-dichlorobenzidine, 3,3'-dimethoxybenzidine, bis(4-amino-3-chlorophenyl)oxide, bis(4-amino-2-chlorophenyl)propane, bis(4-amino-2-chlorophenyl)sulfone, bis(4-amino-3-methoxyphenyl)decane, bis(4-aminophenyl) sulfide, bis(4-aminophenyl) telluride, bis(4-aminophenyl) selenide, bis(4-amino-3-methoxyphenyl) disulfide, 4,4'-methylenebis(2-iodoaniline), 4,4'-methylenebis(2--bromoaniline), 4,4'-methylenebis(2-fluoroaniline), 4-aminophenyl-2-chloroaniline and the like.

[4] The secondary amino group-carrying aromatic polyamine may for example be an aromatic polyamine of the above-mentioned [1] to [3] in which a part or all of —NH$_2$ is replaced with —NH—R' (R' is an alkyl group, such as a lower alkyl group of 1 to 4 carbon atoms including methyl, ethyl and the like) [4,4'-di(methylamino)diphenylmethane, 1-methyl-2-methylamino-4-aminobenzene and the like], polyamide polyamine: a low molecular weight polyamide polyamine obtained by the condensation of a dicarboxylic acid (dicarboxylic acid (dimeric acid and the like) and an excess (2 moles or more per mole of the acid) of a polyamine (above-mentioned alkylene diamine, polyalkylene polyamine and the like), polyether polyamine: hydrogenated cyanoethyl polyether polyol (polyalkylene glycol and the like) and the like.

The polythiol (17) may be a dithiol of 2 to 24 carbon atoms, a 3- to 6- or higher valent polythiol of 5 to 30 carbon atoms and the like.

The dithiol may for example be ethylene dithiol, 1,4-butane dithiol, 1,6-hexane dithiol and the like, The polythiol may for example be Cupkure 3800 (JAPAN EPOXY RESIN), polyvinyl thiol and the like.

Among active hydrogen-containing compounds (β1), those preferred are water, diol (11), polyol (12), dicarboxylic acid (13) and polyamine (16), and those more preferred are water, diol (11), polyol (12) and polyamine (16), with diol (11), polyol (12) and polyamine (16) being especially preferred.

The epoxy resin may be a ring-opening polymerization product of a polyepoxide (18), a polyadduct of a polyepoxide (18) and an active hydrogen-containing compound (β1), a polyepoxide (18) cured with a dicarboxylic acid (13) or a 3- to 4- or higher valent polycarboxylic acid (14) anhydride and the like.

A ring opening reaction and a polyaddition reaction can employ known catalysts and the like.

The preferred polyepoxide (18) has 2 to 6 epoxy groups in its molecule in view of the mechanical properties of a hardened material, although it is not limited particularly as long as it has 2 or more epoxy groups in its molecule.

The epoxy equivalent (molecular weight per epoxy group) of the polyepoxide (18) is preferably 65 to 1000, more preferably 70 to 500, especially 90 to 300. Thus, the upper limit of the epoxy equivalency is preferably 1000, more preferably 500, especially 300, while the lower limit is preferably 65, more preferably 70, especially 90. An epoxy equivalent exceeding this range may results in a looser crosslinking structure which leads to a deterioration of the physical properties of a cured article such as water resistance, chemical resistance and mechanical strength, while an epoxy equivalent less than this range may hardly be available (and also hardly be synthesized).

The polyepoxide (18) may be an aromatic polyepoxide, heterocycle-containing polyepoxide, alicyclic polyepoxide, aliphatic polyepoxide and the like.

The aromatic polyepoxide may be a polyhydric phenol glycidyl ether, polyhydric phenol glycidyl ester, glycidyl aromatic polyamine, glycidylated aminophenol and the like.

The polyhydric phenol glycidyl ether may for example be a bisphenol F diglycidyl ether, bisphenol A diglycidyl ether, bisphenol B diglycidyl ether, bisphenol AD diglycidyl ether, bisphenol S diglycidyl ether, halogenated bisphenol A diglycidyl, tetrachlorobisphenol A diglycidyl ether, catechin diglycidyl ether, resorcinol diglycidyl ether, hydroquinone diglycidyl ether, pyrogallol triglycidyl ether, 1,5-dihydroxynaphthaline diglycidyl ether, dihydroxybiphenyl diglycidyl ether, octachloro-4,4'-dihydroxybiphenyl diglycidyl ether, tetramethylbiphenyl diglycidyl ether, dihydroxynaphthyl-cresol triglycidyl ether, tris(hydroxyphenyl)methanetriglycidyl ether, dinaphthyl triol triglycidyl ether, tetrakis(4-hydroxyphenyl)ethane tetraglycidyl ether, p-glycidylphenyl dimethyl triol bisphenol A glycidyl ether, trismethyl-t-butyl-butylhydroxymethanetriglycidyl ether, 9,9'-bis(4-hydroxyphenyl)fluorene diglycidyl ether, 4,4'-oxybis(1,4-phenylethyl)tetracresol glycidyl ether, 4,4'-oxybis(1,4-phenylethyl) phenylglycidyl ether, bis(dihydroxynaphthalene) tetraglycidyl ether, phenol or cresol novolak resin glycidyl ether, limonene phenol novolak resin glycidyl ether, diglycidyl ether obtained by the reaction between 2 moles of bisphenol A and 3 moles of epichlorohydrin, polyphenol polyglycidyl ether obtained by a condensation reaction of phenol with glyoxazal, glutaraldehyde or formaldehyde, polyphenol polyglycidyl ether obtained from a condensation reaction of resorcin and acetone.

The polyhydric phenol glycidyl ester may for example be diglycidyl phthalate, diglycidyl isophthalate, diglycidyl terephthalate and the like.

The glycidyl aromatic polyamine may for example be N,N-diglycidylaniline, N,N,N',N'-tetraglycidyl xylylene diamine and N,N,N',N'-tetraglycidyldiphenylmethane diamine and the like.

The epoxide may further be a p-aminophenol triglycidyl ether, diglycidylurethane compound obtained by an addition reaction of tolylene diisocyanate or diphenylmethanediisocyanate with glycidol, and diglycidyl ether form of a bisphenol A alkylene oxide (ethylene oxide or propylene oxide 2 to 20 moles) adduct (for example, bisphenol AEO 4-mole adduct diglycidyl ether form and the like).

The heterocyclic polyepoxide may for example be trisglycidyl melamine and the like.

The aliphatic polyepoxide may for example be vinylcyclohexane dioxide, limonene dioxide, dicyclopentadiene dioxide, bis(2,3-epoxycyclopentyl) ether, ethylene glycol bisepoxydicyclopentyl ether, 3,4-epoxy-6-methylcyclohexylmethyl-3',4'-epoxy-6'-methylcyclohexane carboxylate, bis(3,4-epoxy-6-methylcyclohexylmethyl)adipate, bis(3,4-epoxy-6-methylcyclohexylmethyl)butylamine, dimeric acid diglycidyl ester and aromatic polyepoxide nuclear-hydrogenated form (bisphenol F diglycidyl ether hydrogenate form, bisphenol A diglycidyl ether hydrogenated form and the like).

The aliphatic polyepoxy may be an aliphaticpolyhydric alcohol polyglycidyl ether, polyvalent fatty acid polyglycidyl ester, and glycidylaliphaticamine and the like.

The aliphaticpolyhydric alcohol polyglycidyl ether may for example be ethylene glycol diglycidyl ether, propylene glycol diglycidyl ether, tetramethylene glycol diglycidyl ether, 1,6-hexane diol diglycidyl ether, polyethylene glycol diglycidyl ether, polypropylene glycol diglycidyl ether, polytetramethylene glycol diglycidyl ether, neopentylglycol diglycidyl ether, trimethylol propane polyglycidyl ether, glycerol polyglycidyl ether, pentaerythritol polyglycidyl ether, sorbitol polyglycidyl ether and polyglycerol polyglycidyl ether and the like.

The polyvalent fatty acid polyglycidyl ester may for example be diglycidyl oxalate, diglycidyl malate, diglycidyl succinate, diglycidyl glutarate, diglycidyladipate and diglycidyl pimelate and the like.

The glycidylaliphaticamine may for example be N,N,N',N'-tetraglycidylhexamethylene diamine, N,N,N',N'-tetraglycidyl ethylene diamine and the like.

The aliphatic polyepoxide includes diglycidyl ether and glycidyl (meth) acrylate (co)polymers Among those listed above, those employed preferably are aliphatic polyepoxy compounds and aromatic polyepoxy compounds. It is possible to employ two or more inventive polyepoxides.

The number average molecular weight of a resin (a) is preferably 500 to 5,000,000. The upper limit is more preferably 1,000,000, especially 500,000, while the lower limit is more preferably 2,000,, especially 3,000.

A number average molecular weight and a weight average molecular weight can be determined by a gel permeation chromatography (GPC) (THF solvent, standard: polystyrene). Hereinafter a number average molecular weight is abbreviated as Mn, and a weight average molecular weight as Mw.

The SP value of the resin (a) is preferably 7 to 18. The upper limit is more preferably 16, especially 14, while the lower limit is more preferably 8, especially 8.5.

The SP value is calculated by the method described in Polymer Engineering and Science, February, 1974, Vol. 14, No.2, page 147 to 154.

When the resin (a) is a crystalline polymer, the melting point of (a) is preferably 35° C. or higher. The upper limit of the melting point is more preferably 250° C., especially 200° C., while the lower limit is more preferably 40° C., especially 50° C.

The melting point is measured by DSC (temperature raising rate: 20° C./minute).

For the purpose of improving the heat resistance, water resistance, chemical resistance and particle diameter uniformity of the composite resin particle, a crosslinking structure may be introduced into the resin (a). Such a crosslinking structure may be of any crosslinking form such as covalent bond, coordinate bond, ion bond, hydrogen bond and the like.

For separating the resin microparticle (A) from the composite resin particle and obtaining the resin particle (B), it is not preferable to introduce a crosslinking structure into (A).

A method for introducing a crosslinking structure may be any ordinary method.

The acid value of the resin (a) [according to JIS K0070 (1966), hereinafter the same applies] is preferably 300 or less, more preferably 200 or less, especially 50 or less, most preferably 10 or less.

The resin microparticle (A) should have a strength capable of avoiding any destruction by a shear force upon dispersing the resin (b), the precursor (b0) of (b) or their solution, and is preferably hardly water-soluble (solubility in water is preferably 10% or less, more preferably 5% or less, especially 1% or less), hardly swollen by water, hardly dissolved or swollen in the resin (b), the precursor (b0) of (b) or their solution.

For the purpose of suppressing the dissolution and swelling of the resin microparticle (A) in water or an organic solvent employed upon dispersing, it is preferable to adjust the molecular weight (Mn, Mw), SP value, crystallinity and crosslinking structure of the resin (a) appropriately.

The glass transition point (Tg) of the resin (A) is preferably 0 to 300° C. in view of the shape, particle diameter uniformity, powder flawability, heat resistance (during storage) and stress resistance. The upper limit of the (Tg) is more preferably 250° C., especially 200° C., while the lower limit is more preferably 20° C., especially 45° C., and most preferably 50° C.

In addition, the Tg can be determined by DSC (differential scanning calorimetry, temperature raising rate: 20° C./minute).

In addition to the resin (a), an additive (T) (various additives such as a filler, colorant, plasticizer, releasing agent, static charge controller, UV absorber, antioxidant, antistatic agent, flame retardant, antibacterial agent, preservative and the like) can be contained in the resin microparticle (A).

While the amount of the additive (T) may be adjusted as appropriate depending on the respective purpose of use, it is preferably 0.01 to 150% based on the weight of the resin (a). The upper limit of the (T) content is more preferably 100%, especially 80%, while the lower limit is more preferably 0.1%, especially 0.2%.

The filler may for example be a silica, alumina, titanium oxide, barium titanate, magnesium titanate, calcium titanate, strontium titanate, zinc oxide, tin oxide, quartz sand, clay, mica, silicic limestone, kieselguhr, chromium oxide, cerium oxide, chromium oxide, red ocher, antimony trioxide, magnesium oxide, zirconium oxide, barium sulfate, barium carbonate, calcium carbonate, silicon carbide, silicone nitride and the like.

The colorant may be any known dye or pigment such as a carbon black, nigrosine dye, iron black, naphthol yellow S, Hansa yellow (10G, 5G, G), cadmium yellow, yellow iron oxide, yellow ocher, yellow zinc, titanium yellow, polazoyellow, oil yellow, Hansa yellow (GR, A, RN, R), pigment yellow L, benzidine yellow (G, GR), permanent yellow (NCG), vulcan fast yellow (5G, R), tartrazine lake, quinoline yellow lake, Anthrazan yellow BGL, isoindolinone yellow, red ocher, zinc oxide red, zinc oxide vermillion, cadmium red, cadmium mercury red, antimony vermillion, permanent red 4R, Para Red, Phsey red, parachloroorthonitroaniline red, lithol fast scarlet G, brilliant fast scarlet, brilliant carmine BS, permanent red (F2R, F4R, FRL, FRLL, F4RH), fast scarlet VD, Belcan fast Rubine B, brilliant scarlet G, lithol Rubine GX, permanent red F5R, brilliant carmine 6B, Pigment scarlet 3B, bordeaux 5B, toluidine maroon, permanent bordeaux F2K, heliobordeaux BL, bordeaux 10B, Bon maroon light, Bon maroon medium, eosin lake, rhodamine lake B, rhodamine lake Y, alizarin lake, thioindigo red B, thioindigo maroon, oil red, quinacridone red, pyrazolone red, polyazo red, chrome vermillion, benzidine orange, perinone orange, oil orange, cobalt blue, cerulean blue, alkali blue lake, peacock blue lake, victoria blue lake, non-metal phthalocyanine blue, phthalocyanine blue, fast sky blue, indanthrene blue (RS, BC), indigo, ultramarine, prussian blue, anthraquinone blue, fast violet B, methyl violet lake, cobalt purple, manganese purple, dioxane violet, anthraquinone violet, chrome green, zinc green, chromium oxide, viridian, emerald green, pigment green B, naphthol green B, green gold, acid green lake, malachite green lake, phthalocyanine green, anthraquinone green, titanium green, zinc powder, Lithobon as well as mixtures thereof.

The plasticizer may for example be the following (V1) to (V5) as well as mixtures thereof although it is not particularly limited.

(V1) A phthalate of 8 to 60 carbon atoms [dibutyl phthalate, dioctyl phthalate, butylbenzyl phthalate, diisodecyl phthalate and the like].

(V2) An aliphatic dibasic acid ester of 6 to 60 carbon atoms [di-2-ethylhexyl adipate, 2-ethylhexyl sebacate, and the like].

(V3) A trimellitate of 10 to 70 carbon atoms [tri-2-ethylhexyl trimellitate, trioctyl trimellitate and the like].

(V4) A phosphate of 6 to 60 carbon atoms [triethyl phosphate, tri-2-ethylhexyl phosphate, tricrezol phosphate and the like].

(V5) a fatty acid ester of 8 to 50 carbon atoms [butyl oleate and the like].

Among the plasticizers, (V1), (V2), (V3) and (V4) are preferred, and (V1), (V2) and (V4) are more preferred, with (V1) and (V4) being particularly preferred.

As the releasing agent, a wax and a silicone oil whose dynamic viscosity at 25° C. is 30 to 100,000 cSt.

The wax may be any known substance, including a polyolefin wax (polyethylene wax, polypropylene wax and the like); long chain hydrocarbon (paraffin wax, Sazol wax and the like); carbonyl group-containing wax and the like. Among these, a carbonyl group-containing wax is preferred. A carbonyl group-containing wax may for example be a polyalkanoic acid ester (carnauba wax, Montan wax, trimethylol propane tribehenate, pentaerythritol tetrabehenate pentaerythritol diacetate dibehenate, glycerin tribehenate, 1,18-octadecanediol distearate and the like); polyalkanol ester (tristearyl trimellitate, distearyl maleate and the like); polyalkanoic acid amide (ethylene diamine dibehenylamide and the like); polyalkylamide (trimellitic tristearylamide and the like); dialkyl ketone (distearyl ketone and the like) and the like. Among these carbonyl group-containing waxes, one preferred is a polyalkanoic acid ester.

The static charge controller may be any known substance, including a nigrosine-based dye, triphenylmethane-based dye, chromium-containing metal complex dye, molybdenate chelate pigment, rhodamine-based dye, alkoxy-based amine, quaternary ammonium salt (including fluorine-modified quaternary ammonium salt), alkylamide, phosphorus element or compound, tungsten element or compound, fluorine-based activating agent, metal salicylate, metal salt of a salicylic acid derivative and the like. Typically, a nigrosine-based dye Bontron 03, a quaternary ammonium salt Bontron P-51, a metal-containing azo dye Bontron S-34, an oxynaphthoic acid-based metal complex E-82, a salicylic acid-based metal complex E-84, a phenol-based condensate E-89 (produced by ORIENT KAGAKU KOGYO), quaternary ammonium salt molybdenum complexes TP-302 and TP-415 (produced by HODOGAYA KAGAKU KOGYO), a quaternary ammonium salt Copy Charge PSY VP2038, a triphenylmethane derivative Copy Blue PR, quaternary ammonium salts Copy Charge NEG VP2036, Copy Charge NX VP434 (produced by Hoechst), LRA-901, a boron complex LR-147 (produced by Japan Carlit Co., Ltd), copper phthalocyanine, perylene, quinacridone, azo-based pigment, other polymeric compounds having functional groups such as sulfo group, carboxyl group, quaternary ammonium salt and the like.

The method for producing the resin microparticle (A) may for example be the methods [1] to [8] described below, although it is not limited particularly. In the methods [1] to [8], the procedure for obtaining an aqueous dispersion of (A) is discussed, but the aqueous dispersion of (A) can be employed as it is for producing an inventive composite resin particle, and the separation only of (A) from the aqueous dispersion or the separation of (A) in the course of preparing the aqueous dispersion is also possible. For such a separation, a filtration, decantation and centrifugation can be employed.

[1] In the case of a vinyl resin, a monomer is used as a starting material to effect polymerization reaction such as suspension polymerization, emulsion polymerization, seed polymerization or dispersion polymerization in the presence of a polymerization catalyst to produce an aqueous dispersion of the resin microparticle (A) directly.

[2] In the case of a polyaddition resin or condensation resin such as a polyester, polyurethane and epoxy resin, the precursor (a0) of the resin (a) [for example, the above-mentioned monomer such as the diol (11), polyol (13), dicarboxylic acid (14), polyisocyanate (15), polyamine (16), polythiol (17), polyepoxide (18) and the like, as well as a reaction product of two or more molecule of said monomer (a reaction product of same kind of monomers or a reaction product of two or more different kinds of monomers) which is an oligomer having an Mn of 1,000 or less] or a solution of the precursor (a0) is dispersed in an aqueous solvent in the presence of a dispersing agent, and then heated or supplemented with a curing agent (a compound having in its molecule at least two functional groups capable of reacting with the precursor), whereby effecting the curing to produce the aqueous dispersion of the resin microparticle (A).

[3] In the case of a polyaddition resin or condensation resin such as a polyester, polyurethane and epoxy resin, a suitable emulsifier is dissolved in the precursor (a0) (monomer, oligomer and the like) or a solution of (a0) (preferably liquid, may be fluidized by heating) and then water is added to effect a phase inversion emulsification.

[4] The resin (a) which has previously been produced by a polymerization reaction (any polymerization reaction mode such as addition polymerization, ring-opening polymerization, polyaddition, addition condensation and polycondensation; hereinafter the same applies) is ground by a microgrinder such as mechanical rotary grinder or jet grinder and then sieved to obtain the microparticle resin (A) which is then disperse in water in the presence of a suitable dispersing agent.

[5] A solution of the resin (a) produced beforehand by polymerization reaction is sprayed as a mist to remove the solvent from the solution of the resin (a) to obtain the resin microparticle (A), which is then dispersed in water in the presence of a suitable dispersing agent.

[6] A solution of the resin (a) produced beforehand by polymerization reaction is combined with a poor solvent [a solvent which doesn't dissolve 1% or more of the resin (a) at 25° C.] or a solution of the resin (a) which has previously been dissolved in a solvent by heating is then cooled to precipitate the resin microparticle and then the solvent is removed to obtain the resin microparticle (A), which is then dispersed in water in the presence of a suitable dispersing agent.

[7] A solution of the resin (a) prepared beforehand by polymerization reaction is dispersed in an aqueous solvent in the presence of a suitable dispersing agent and then subjected to heating or reduced pressure to remove the solvent.

[8] In a solution of the resin (a) prepared beforehand by polymerization reaction, a suitable emulsifier is dissolved and then water is added to effect phase inversion emulsification, and then the mixture is subjected to heating or reduced pressure to remove the solvent.

Among the methods [1] to [8] described above, the methods [1] to [3], [7] and [8] are preferred, and [1] to [3] and [7] are more preferred, and [2], [3] and [7] are especially preferred.

In such methods, the concentration of a solid in an aqueous dispersion is preferably 1 to 70%, more preferably 5 to 65%, especially 10 to 60%.

An emulsifier and a dispersing agent employed in the methods [1] to [8] may be any known surfactant (S) or water-soluble polymer (T).

When the surfactant (S) is employed, the amount is preferably 0.0001 to 50% based on the weight of (a) and (a0). The upper limit is more preferably 0.4%, especially 0.3%, while the lower limit is more preferably 0.0005%, especially 0.001%.

When the water-soluble polymer (T) is employed, the amount is preferably 0.005 to 0.6% based on the weight of (a) and (a0). The upper limit is more preferably 0.4%, especially 0.3%, while the lower limit is more preferably 0.01%, especially 0.02%.

As an auxiliary agent for the emulsification and the dispersion, a solvent (U) and/or a plasticizer (V) may also be employed.

When the solvent (U) is employed, the amount is preferably 0.001 to 0.5% based on the weight of (a) and (a0). The upper limit is more preferably 0.4%, especially 0.3%, while the lower limit is more preferably 0.002%, especially 0.01%.

When the plasticizer (V) is employed, the amount is preferably 0.01 to 0.3% based on the weight of (a) and (a0). The upper limit is more preferably 0.25%, especially 0.2%, while the lower limit is more preferably 0.02%, especially 0.03%.

The solvent (U) and/or plasticizer (V) may be added to water or to the resin (a) if desired upon emulsifying and dispersing.

The surfactant (S) may be an anionic surfactant (S-1), cationic surfactant (S-2), amphoteric surfactant (S-3), nonionic surfactant (S-4) and the like. Two or more of the surfactants (S) may be used in combination.

The anionic surfactant (S-1) includes carboxylic acids or their salts, sulfates, carboxymethylation product salts, sulfonates, phosphate esters.and the like.

The carboxylic acid or its salt may be a saturated or unsaturated fatty acid of 8 to 22 carbon atoms or its salt, such as capric acid, lauric acid, myristic acid, palmitic acid, stearic acid, arachidic acid, behenic acid, oleic acid, linoleic acid, ricinolic acid as well as a mixture of higher fatty acids obtained by saponifying palm oil, palm kernel oil, rice bran oil, beef tallow and the like.

Salts of those mentioned above may for example be the sodium salts, potassium salts, amine salts, ammonium salts, quaternary ammonium salts, alkanolamine salts (monoethanolamine salts, diethanolamine salts, triethanolamine salts and the like) and the like.

The sulfate ester may for example be a higher alcohol sulfate salt (sulfate salt of an aliphatic alcohol of 8 to 18 carbon atoms), higher alkyl ether sulfate salt (sulfate salt of 1 to 10-mole adduct of EO or PO of an aliphatic alcohol of 8 to 18 carbon atoms), sulfated oil (sulfated and neutralized naturally occurring unsaturated fat or unsaturated wax of 12 to 50 carbon atoms), sulfated fatty acid ester (sulfated and neutralized lower alcohol (1 to 8 carbon atoms) ester of a unsaturated fatty acid (6 to 40 carbon atoms)), sulfated olefin (sulfated and neutralized olefin of 12 to 18 carbon atoms) and the like.

The salt may for example be a sodium salt, potassium salt, amine salt, ammonium salt, quaternary ammonium salt, alkanolamine salt (monoethanolamine salt, diethanolamine salt, triethanolamine salt and the like) and the like.

The higher alcohol sulfate salt may for example be an octyl alcohol sulfate salt, decyl alcohol sulfate salt, lauryl alcohol sulfate salt, stearyl alcohol sulfate salt, sulfate salt of an alcohol synthesized using a Ziegler catalyst (for example, trade name: ALFOL 1214: produced by CONDEA), sulfate salt of an alcohol synthesized by an oxo method (for example, trade name: Dobanol 23, 25, 45, Diadol 115-L, 115H, 135: MITSUBISHI KAGAKU, trade name: Tridecanol: KYOWA HAKKO, trade name: Oxocol 1213, 1215, 1415: NISSAN KAGAKU) and the like.

The higher alkyl ether sulfate salt may for example be a lauryl alcohol EO 2-mole adduct sulfate salt, octyl alcohol EO 3-mole adduct sulfate salt and the like.

The sulfated oil may for example be a sulfated salt of castor oil, peanut oil, olive oil, rapeseed oil, beef tallow, sheep fat and the like.

The sulfated fatty acid ester may for example be a sulfated salt of butyl oleate, butyl ricinoleate and the like.

The sulfated olefin may for example be one having a trade name: T-POLE (Shell) and the like.

The carboxymethylated product salt may be a carboxylmetylated product salt of an aliphatic alcohol of 8 to 16 carbon atoms, carboxylmetylated product salt of an EO or PO 1 to 10-mole adduct of an aliphatic alcohol of 8 to 16 carbon atoms and the like.

The carboxymethylated product salt of an aliphatic alcohol may for example be carboxymethylated sodium salt of octyl alcohol, carboxymethylated sodium salt of decyl alcohol, carboxymethylated sodium salt of lauryl alcohol, carboxymethylated sodium salt of Dobanol 23, carboxymethylated sodium salt of tridecanol and the like.

The carboxylmetylated product salt of an EO 1 to 10-mole adduct of an aliphatic alcohol may for example be a carboxymethylated sodium salt of octyl alcohol EO 3-mole adduct, carboxymethylated sodium salt of lauryl alcohol EO 4-mole adduct, carboxymethylated sodium salt of Dobanol 23 EO 3-mole adduct, carboxymethylated sodium salt of tridecanol EO 5-mole adduct and the like.

The sulfonate may be (d1) an alkylbenzene sulfonate, (d2) an alkylnaphthalene sulfonate, (d3) a sulfosuccinic acid diester salt, (d4) an α-olefin sulfonate, (d5) an Igepon T-type and (d6) a sulfonate of other aromatic ring-containing compound and the like. The alkylbenzene sulfonate (d1) may for example be sodium dodecylbenzenesulfonate and the like.

The alkylnaphthalene sulfonate (d2) may for example be sodium dodecylnaphthalenesulfonate and the like.

The sulfosuccinic acid diester salt (d3) may for example be di-2-ethylhexyl sulfosuccinate sodium salt and the like.

The sulfonate of an aromatic ring-containing compound may for example be a monosulfonate or disulfonate of an alkylated diphenyl ether, styrene-derivatized phenol sulfonate and the like.

The phosphate salt may be (e1) a higher alcohol phosphate salt, (e2) a higher alcohol EO-adduct phosphate salt and the like.

The higher alcohol phosphate salt (e1) may for example be lauryl alcohol monophosphate disodium salt, lauryl alcohol diphosphate sodium salt and the like.

The higher alcohol EO-adduct phosphate salt may for example be oleyl alcohol EO 5-mole adduct monophosphate disodium salt and the like.

The cationic surfactant (S-2) may be a quaternary ammonium salt type surfactant, amine salt type surfactant and the like.

The quaternary ammonium salt type surfactant may be obtained by a reaction of a tertiary amine of 3 to 40 carbon atom and a quaternizing agent (an alkylating agent such as methyl chloride, methyl bromide, ethyl chloride, benzyl chloride, dimethyl sulfuric acid as well as EO), including lauryltrimethylammonium chloride, didecyldimethylammonium chloride, dioctyldimethylammonium bromide, stearyltrimethylammonium bromide, lauryldimethylbenzylammonium chloride (benzalkonium chloride), cetylpyridinium chloride, polyoxyethylene trimethylammonium chloride, stearamideethyldiethylmethylammonium methosulfate and the like.

The amine salt type surfactant is obtained for example by neutralizing a primary to tertiary amine with an inorganic acid (hydrochloric acid, nitric acid, sulfuric acid, hydroiodic acid, phosphoric acid, perchloric acid, and the like), or an organic acid (acetic acid, formic acid, oxalic acid, lactic acid, gluconic acid, adipic acid, alkylphosphoric acid of 2 to 24 carbon atoms, malic acid, citric acid and the like).

The primary amine salt type surfactant may for example be an inorganic acid salt or organic acid salt of an aliphatic higher amine of 8 to 40 carbon atoms (a higher amine such as laurylamine, stearylamine, cetylamine, hardened beef tallow amine, rosin amine and the like), as well as a higher fatty acid (of 8 to 40 carbon atoms, such as stearic acid, oleic acid) salt of a lower amine (of 2 to 6 carbon atoms) and the like.

The secondary amine salt type surfactant may for example be an inorganic acid salt or organic acid salt of an EO adduct of an aliphatic amine of 4 to 40 carbon atoms.

The tertiary amine salt type surfactant may for example be an inorganic acid salt or organic acid salt of an aliphatic amine of 4 to 40 carbon atoms (triethylamine, ethyldimethylamine, N,N,N',N'-tetramethylethylenediamine and the like), an aliphatic amine (2 to 40 carbon atoms) EO (2 moles or more) adduct, an alicyclic amine of 6 to 40 carbon atoms (N-methylpyrrolidine, N-methylpiperidine, N-methylhexamethyleneimine, N-methylmorpholin, 1,8-diazabicyclo(5,4,0)-7-undecene and the like), a nitrogen-containing heterocyclic aromatic amine of 5 to 30 carbon atoms (4-dimethylaminopyridine, N-methylimidazole, 4,4'-dipyridyl and the like), as well as an inorganic acid salt or organic acid salt of a tertiary amine such as triethanolamine monostearate, stearamide ethyldiethylmethyl ethanolamine and the like.

The amphoteric surfactant (S-3) may be a carboxylic acid type amphoteric surfactant, sulfate salt type amphoteric surfactant, sulfonate type amphoteric surfactant, phosphate salt type amphoteric surfactant and the like.

The carboxylate salt type may be an amino acid type amphoteric surfactant, betaine type amphoteric surfactant, imidazoline type amphoteric surfactant and the like. The amino acid type amphoteric surfactant is an amphoteric surfactant having both of an amino group and a carboxylic group in its molecule and may for example be a compound represented by general formula (2):

[R—NH—(CH$_2$)$_n$—COO]$_m$M  (2)

wherein R is a monovalent hydrocarbon group; n is 1 or 2; m is 1 or 2; M is a hydrogen ion, alkaline metal ion, alkaline earth metal ion, ammonium cation, amine cation, alkanolamine cation and the like.

The amphoteric surfactant represented by general formula (2) may for example be an alkyl (6 to 40 carbon atoms) aminopropionic acid type amphoteric surfactant (sodium stearylaminopropionate, sodiumlaurylaminopropionate and the like); alkyl (4 to 24 carbon atoms) aminoacetic acid type amphoteric surfactant (sodium laurylaminoacetate and the like) and the like.

The betaine type amphoteric surfactant is an amphoteric surfactant having a quaternary ammonium salt type cation moiety and a carboxylic acid type anion moiety in its molecule, and may for example be an alkyl (6 to 40 carbon atoms) dimethylbetaine (stearyldimehylaminoacetatebetaine,lauryldimehylaminoacetat ebetaine and the like), amidebetaine of 6 to 40 carbon atoms (palm oil fatty acid amide propylbetaine and the like), an alkyl (6 to 40 carbon atoms) dihydroxyalkyne (6 to 40 carbon atoms) betaine (lauryldihydroxyethylbetaine and the like) and the like.

The imidazoline type amphoteric surfactant may for example be an imidazoline ring-carrying amphoteric surfactant having a cation moiety and a carboxylate type anion moiety, such as 2-undecyl-N-carboxymethyl-N-hydroxyethylimidazolinium betaine and the like.

Other amphoteric surfactants include glycine type amphoteric surfactants such as sodium lauroyl glycine, sodium lauryldiaminoethylglycine, lauryldiaminoethylglycine hydrochloride, dioctyldiaminoethylglycine hydrochloride and the like; sulfobetaine type amphoteric surfactants such as pentadecylsulfotaurine, sulfonate type amphoteric surfactants, phosphate salt type amphoteric surfactants and the like.

The nonionic surfactant (S-4) may be an alkylene oxide-added nonionic surfactant, polyhydric alcohol type nonionic surfactant and the like.

The alkylene oxide-added nonionic surfactant can be obtained by adding an alkylene oxide (2 to 20 carbon atoms) directly to a higher alcohol of 8 to 40 carbon atoms, a higher fatty acid of 8 to 40 carbon atoms or an alkylamine of 8 to 40 carbon atoms, or by reacting a higher fatty acid with a polyalkylene glycol obtained by adding an alkylene oxide to glycol, or by adding an alkylene oxide to an esterified product obtained by reacting a polyhydric alcohol with a higher fatty acid, or by adding an alkylene oxide to a higher fatty acid amide.

The alkylene oxide may for example be EO, PO and butylene oxide.

Among those listed above, EO and a random or block copolymer of EO and PO are preferred.

The molar number of an alkylene oxide added is preferably 10 to 50 moles, and among such alkylene oxides, one in which 50 to 100% corresponds to EO is preferred.

The alkylene oxide-added nonionic surfactant may for example be an oxyalkylene alkyl ether (alkylene of 2 to 24 carbon atoms, alkyl of 8 to 40 carbon atoms) (octyl alcohol EO 20-mole adduct, lauryl alcohol EO 20-mole adduct, stearyl alcohol EO 10-mole adduct, oleyl alcohol EO 5-mole adduct, lauryl alcohol EO 10-mole and PO 20-mole block adduct and the like); polyoxyalkylene higher fatty acid ester (alkylene of 2 to 24 carbon atoms, higher fatty acid of 8 to 40 carbon atoms) (stearic acid EO 10-mole adducts, lauric acid EO 10-mole adducts and the like);

polyoxyalkylene polyhydric alcohol higher fatty acid ester (alkylene of 2 to 24 carbon atoms, polyhydric alcohol of 3 to 40 carbon atoms, higher fatty acid of 8 to 40 carbon atoms) (polyethylene glycol (polymerization degree: 20) dilaurate, polyethylene glycol (polymerization degree: 20) dioleate, polyethylene glycol (polymerization degree: 20) distearate and the like); polyoxyalkylene alkylphenyl ether (alkylene of 2 to 24 carbon atoms, alkyl of 8 to 40 carbon atoms) (nonylphenol EO 4-mole adduct, nonylphenol EO 8-mole and PO-20 mole block adduct, octylphenol EO 10-mole adduct, bisphenol A EO 10-mole adduct, dinonylphenol EO 20-mole adduct, styrene-derivatized phenol EO 20-mole adduct and the like); polyoxyalkylenealkyl aminoether (alkylene of 2 to 24 carbon atoms, alkyl of 8 to 40 carbon atoms) (laurylamine EO 10-mole adduct, stearylamine EO 10-mole adduct and the like); polyoxyalkylene alkanolamide (alkylene of 2 to 24 carbon atoms, amide (acyl moiety) of 8 to 24 carbon atoms) (hydroxyethyllauric acid amide EO 10-mole adduct, hydroxypropyloleic acid amide EO 20-mole adduct, dihydroxyethyllauric acid amide EO 10-mole adduct and the like) and the like.

The polyhydric alcohol type nonionic surfactant may be a polyhydric alcohol fatty acid ester, polyhydric alcohol fatty acid ester alkylene oxide adduct, polyhydric alcohol alkyl ether, polyhydric alcohol alkyl ether alkylene oxide adduct and the like. The number of the carbon atoms in the polyhydric alcohol is 3 to 24, the number in the fatty acid is 8 to 40, and the number in the alkylene oxide is 2 to 24.

The polyhydric alcohol fatty acid ester may for example be pentaerythritol monolaurate, pentaerythritol monooleate, sorbitan monolaurate, sorbitan monostearate, sorbitan monolaurate, sorbitan dilaurate, sorbitan dioleate, sucrose monostearate and the like.

The polyhydric alcohol fatty acid ester alkylene oxide adduct may for example be ethylene glycol monooleate EO 10-mole adduct, ethylene glycol monostearate EO 20-mole adduct, trimethylolpropane monostearate EO 20-mole and PO 10-mole random adduct, sorbitan monolaurate EO 10-mole adduct, sorbitan monostearate EO 20-mole adduct, sorbitan distearate EO 20-mole adduct, sorbitan dilaurate EO 12-mole and PO 24-mole random adduct and the like.

The polyhydric alcohol alkyl ether may for example be pentaerythritol monobutyl ether, pentaerythritol monolauryl ether, sorbitan monomethyl ether, sorbitan monostearyl ether, methyl glycoside, lauryl glycoside and the like.

The polyhydric alcohol alkyl ether alkylene oxide adduct may for example be sorbitan monostearyl ether EO 10-mole adduct, methyl glycoside EO 20-mole and PO 10-mole random adduct, lauryl glycoside EO 10-mole adduct, stearyl glycoside EO 20-mole and PO 20-mole random adduct and the like The water-soluble polymer (T) may for example be a cellulose (methyl cellulose, ethyl cellulose, hydroxyethyl cellulose, ethylhydroxyethyl cellulose, carboxymethyl cellulose, hydroxpropyl cellulose, as well as saponified products thereof, cationized cellulose and the like), gelatin, starch, dextrin, gum arabic, chitin, chitosan, polyvinyl alcohol, polyvinyl pyrrolidone, polyethylene glycol, polyethylene imine, polyacrylamide, acrylic acid (salt)-containing polymer (sodium polyacrylate, potassium polyacrylate, ammonium polyacrylate, polyacrylic acid neutralized partially with sodium hydroxide, sodium acrylate-acrylate copolymer), styrene-maleic anhydride copolymer neutralized (partially) with sodium hydroxide, water-soluble polyurethane (reaction product of polyethylene glycol, polycaprolactonediol and the like with polyisocyanate, and the like) and the like.

Among water-soluble polymers, those preferred are celluloses, starches, polyvinyl alcohols, polyvinyl pyrrolidones, polyethylene glycols, acrylic acid (salts)-containing polymers.

The solvent (U) may for example be an aromatic hydrocarbon solvent (toluene, xylene, ethylbenzene, tetralin and the like); aliphatic or alicyclic hydrocarbon solvent (n-hexane, n-heptane, mineral split, cyclohexane and the like); halogenated hydrocarbon solvent (methyl chloride, methyl bromide, methyl iodide, methylene dichloride, carbon tetrachloride, trichloroethylene, perchloroethylene and the like); ester or ester ether solvent (ethyl acetate, butyl acetate, methoxybutyl acetate, methyl cellosolve acetate, ethyl cellosolve acetate and the like); ether solvent (diethyl ether, tetrahydrofuran, dioxane, ethyl cellosolve, butyl cellosolve, propylene glycol monomethyl ether and the like); ketone solvent (acetone, methyl ethyl ketone, methyl isobutyl ketone, di-n-butyl ketone, cyclohexanone and the like); alcohol solvent (methanol, ethanol, n-propanol, isopropanol, n-butanol, isobutanol, t-butanol, 2-ethylhexyl alcohol, benzyl alcohol and the like); amide solvent (dimethyl formamide, dimethyl acetamide and the like); sulfoxide solvent (dimethyl sulfoxide and the like); heterocyclic compound solvent (N-methylpyrrolidone and the like); as well as solvent mixtures of two or more of those listed above.

Among the solvents, those preferred in view of efficiency in removing the solvents are aromatic hydrocarbon solvents, halogen solvents, ester or ester ether solvents, ketone solvents and alcohol solvents, with ester or ester ether solvents, ketone solvents and alcohol solvents being more preferred.

The plasticizer (V) is not limited particularly, and may be those listed as (V1) to (V5) above as well as mixtures thereof. The preferred ranges are also as described above.

The resin particle (B) contains the resin (b).

Such a resin (b) may be any known resin similarly to the resin (a), and those exemplified typically are also similar to those exemplified as (a).

The resin (b) may appropriately be selected in view of the application and the purpose of use, and may preferably be a vinyl resin, polyurethane, epoxy resin, polyester, polyamide, polyimide, silicone resin, phenol resin, melamine resin, urea resin as well as mixtures of two or more, and more preferably a vinyl resin, polyurethane, epoxy resin, polyester, polyamide, polyimide and mixtures of two or more, and especially a vinyl resin, polyurethane, epoxy resin, polyester and mixtures of two or more, most preferably a polyurethane, epoxy resin, polyester and mixtures of two or more.

The Mn, Tg, melting point if any, and SP value of the resin (b) can appropriately be adjusted within a preferred range depending on the application.

For example, when the composite resin particle or the resin particle (B) is employed as a slush molding resin or powder paint, then the Mn of the resin (b) is preferably 2,000 to 500,000. The upper limit of the Mn is more preferably 200,000, especially 100,000, while the lower limit is more preferably 2,500, especially 4,000.

When (b) has a melting point, the melting point (b) is preferably 0 to 250° C. The upper limit is more preferably 200° C., especially 180° C., while the lower limit is more preferably 35° C., especially 40° C.

The Tg of (b) is preferably −60 to 100° C. The upper limit of the Tg is more preferably 80° C., especially 70° C., while the lower limit is more preferably −40° C., especially −30° C.

The SP value of (b) is preferably 7 to 18. The upper limit of the SP value is more preferably 16, especially 14, while the lower limit is more preferably 8, especially 9.

When using as a spacer for producing an electronic part such as a liquid crystal display or as a standard particle of an electronic measurement device, the Mn of (b) is preferably 10,000 to 10,000,000. The upper limit of the Mn is more preferably 2,000,000, especially 1,000,000, while the lower limit is more preferably 15,000, especially 20,000.

When (b) has a melting point, the melting point is preferably 50 to 300° C. The upper limit of the melting point is more preferably 250° C., especially 240° C., while the lower limit is more preferably 80° C., especially 100° C.

The Tg of (b) is preferably 0 to 250° C. The upper limit of the Tg is more preferably 200° C., especially 150° C., while the lower limit is more preferably 20° C., especially 35° C.

The SP value of (b) is preferably 8 to 18. The upper limit of the SP value is more preferably 16, especially 14, while the lower limit is more preferably 9, especially 9.5.

When using as a toner employed for example in an electrophotography, electrostatic recording and electrostatic printing, the Mn of (b) is preferably 1,000 to 5,000,000. The upper limit of the Mn is more preferably 500,000, especially 100,000, while the lower limit is preferably 1,000, more preferably 2,000, particularly 3000.

When (b) is a resin having a melting point, the melting point is preferably 20 to 200° C. The upper limit is more preferably 90° C., especially 80° C., while the lower limit is more preferably 30° C., especially 40° C.

The Tg of (b) is preferably 20 to 200° C. The upper limit of the Tg is more preferably 90° C., especially 80° C., while the lower limit is more preferably 30° C., especially 40° C.

The SP value of (b) is preferably 8 to 16. The upper limit of the SP value is especially 14, while the lower limit is more preferably 8.5, especially 9.

An acid value of resin (b) is preferably 0 to 300.

When using the composite resin particle as an additive for a paint or coating, or as a powder coating, slush molding resin or hot melt adhesive, then the upper limit of the acid value of (b) is preferably 200, more preferably 100, and the lower limit is preferably 1.

When using as a toner employed for example in an electrophotography, electrostatic recording and electrostatic printing, in view of the electrostatic charge profile or the performance of fixation on a paper, then the upper limit of the acid value of (b) is more preferably 200, especially 100, and most preferably 50, while the lower limit is more preferably 1, especially 3, most preferably 5.

In the second aspect of the present invention, one having an acid value of 5 to 100 is employed especially as (b). The lower limit is preferably 7, more preferably 9, while the upper limit is preferably 80, more preferably 60, especially 50.

In the second aspect of the present invention, (b) has an acidic functional group at its molecular terminal, or on its side chain, and such an acidic functional group may for example be a carboxyl group (—COOH), sulfo group (—SO$_3$H), phosphono group {—PO(OH)$_2$}, sulfamate-derived group {—N(SOH)$_3$—} and the like. Among these, a carboxyl group, sulfo group and phosphono group are preferred, with a carboxyl group and sulfo group being more preferred. By introducing such an acidic functional group into the molecule to achieve an acid value within the range specified above, the adhesion (adhesiveness) to a substrate such as metal, wood and paper is substantially improved.

While a method for imparting the resin (b) with an acid value within the range specified above is not limited particularly, the following methods [1] and [2] can be mentioned.

[1] A method in which an acidic group-containing monomer is reacted simultaneously with the resin synthesis.

[2] A method in which the functional group at the terminal and/or on the side chain of the resin (b) is modified with an acidic group-containing compound.

Typically, for example, the following two can be mentioned as methods for imparting a vinyl resin with an acid value.

[1]-1: A method in which an acidic group-containing vinyl monomer and other vinyl monomers are employed as starting material to effect polymerization reaction such as suspension polymerization, emulsion polymerization, dispersion polymerization and the like in the presence of a polymerization catalyst to obtain the resin (b).

[2]-1: A method in which a vinyl monomer having a functional group capable of reacting with a carboxylic acid such as a hydroxyl group, amino group, epoxy group and the like and other vinyl monomers are employed as starting material to effect polymerization reaction such as bulk polymerization, solution polymerization, suspension polymerization, emulsion polymerization, dispersion polymerization and the like in the presence of a polymerization catalyst to obtain a resin, whose functional group is then further reacted with a polycarboxylic acid, sulfocarboxylic acid or acid anhydride to introduce an acidic functional group into the resin.

The acidic group-containing monomer which can be employed in Method [1]-1 may for example be the above-mentioned (2) carboxyl group-containing vinyl monomer, (3) sulfo group-containing vinyl monomer, (4) phosphono group-containing vinyl monomer and the like, while the other vinyl monomers may for example be the above-mentioned vinyl monomers other than the above-mentioned acidic group-containing vinyl monomers.

Among these acidic group-containing monomers, those preferred are (2) carboxyl group-containing vinyl monomers and (3) sulfo group-containing vinyl monomers, especially (2) carboxyl group-containing vinyl monomers.

The polymerization reaction temperature is 0 to 180° C., preferably 30 to 150° C., more preferably 50 to 120° C.

As a solvent, an aromatic solvent (toluene, xylene and the like), ketone-based solvent (acetone, methyl isobutyl ketone and the like), ester-based solvent (ethyl acetate, butyl acetate and the like), ether-based solvent (diethyl ether, dibutyl ether and the like), alcoholic solvent (ethanol, isopropanol and the like) can be employed as appropriate on the basis of the polymerization reaction.

The vinyl monomer having a functional group capable of reacting with a carboxylic acid such as a hydroxyl group, amino group, epoxy group and the like employed in Method [2]-1 may for example be the above-mentioned (5) hydroxyl group-containing vinyl monomer, (6-1) amino group-containing vinyl monomer, (7) epoxy group-containing vinyl monomer of 6 to 18 carbon atoms and the like, while other monomers may for example be the above-mentioned vinyl monomers other than those listed above.

The acid anhydride may for example be anhydrides of the above-mentioned dicarboxylic acid (13) and polycarboxylic acid (14).

The sulfocarboxylic acid may for example be those described in JP-B-45-10794 and U.S. Pat. No. 2,176,423.

A preferred vinyl monomer having a functional group capable of reacting with a carboxylic acid includes a hydroxy group-containing vinyl monomer, (7) epoxy group-containing vinyl monomer of 6 to 18 carbon atoms.

As a method for imparting a polyurethane with an acid value, the following two methods can be mentioned.

[1]-2: A method in which an acidic group-containing polyol, polyol, polyisocyanate are employed as starting materials to conduct polyaddition reaction if necessary using a known urethane-forming catalyst such as dibutyl tin oxide in the absence or presence of a solvent to obtain the resin (b).

[2]-2: A method in which a polyol, polyisocyanate are employed as starting materials to conduct polyaddition reaction if necessary using a known urethane-forming catalyst such as dibutyl tin oxide in the absence or presence of a solvent to obtain a polyurethane having a hydroxyl group at the terminal or on the side chain, and then the hydroxyl group is reacted with a polycarboxylic acid or acid anhydride to introduce an acidic functional group.

A polyol, polyisocyanate and acid anhydride employed in Methods [1]-2 and [2]-2 may for example be those similar to the above-mentioned diol (11) and 3- to 8- or higher valent polyol (12), polyisocyanate (15), anhydride of dicarboxylic acid (14) and 3- to 4- or higher valent polycarboxylic acid (14), and the preferred ones are also similar to those listed above.

An acidic group-containing polyol employed in Method [1]-2 may for example be a carboxylic acid of 3 to 8 carbon atoms having 2 to 3 alkylol groups, and those which can be mentioned to be preferred are dimethylol propionic acid, dimethylol butanoic acid.

As a method for imparting an epoxy resin with an acid value, the following two method can be mentioned.

[1]-3: A method in which a polyepoxide and an excess of a polycarboxylic acid or acid anhydride and/or a sulfonic acid group-containing polycarboxylic acid are employed as starting materials to conduct polyaddition reaction if necessary using a known epoxy catalyst such as a tertiary amine in the absence or presence of a solvent to obtain the resin (b) having a carboxylate group at the terminal and/or a sulfonic acid group on the side chain.

[2]-3: A method in which an excess of a polyepoxide and an active hydrogen compound are employed as starting materials to conduct polyaddition reaction if necessary using a known epoxy catalyst such as a tertiary amine in the absence or presence of a solvent to obtain a resin having an epoxy group at the terminal, and then the epoxy group is reacted with a polycarboxylic acid, sulfocarboxylic acid or acid anhydride to introduce an acidic functional group.

A polyepoxide, acid anhydride, active hydrogen compound employed in Methods [1]-3, [2]-3 may for example be those similar to the above-mentioned polyepoxide (18), acid anhydride of a dicarboxylic acid (14) and 3- to 4- or higher valent polycarboxylic acid (14), active hydrogen compound (D), and the preferred ones are also similar to those listed above. As the polycarboxylic acid containing a sulfonic acid group may for example be 4-sulfoisophthalic acid, sulfosuccinic acid and the like.

As a method for imparting a polyester with an acid value, the following two methods can be mentioned.

[1]-4: A method in which a polyol and an excess of a polycarboxylic acid and/or a sulfonic acid group-containing polycarboxylic acid are employed as starting materials to conduct polycondensation reaction if necessary using a known esterifying catalyst such as dibutyl tin oxide, potassium titanyl oxalate in the absence or presence of a solvent to obtain the resin (b) having a carboxylate group at the terminal and/or a sulfonic acid group on the side chain.

[2]-4: A method in which an excess of a polyol and a polycarboxylic acid are employed as starting materials to conduct polycondensation reaction if necessary using a known esterifying catalyst such as dibutyl tin oxide, potassium titanyl oxalate in the absence or presence of a solvent to obtain a polyester having a hydroxyl group at the terminal, and then the hydroxyl group is reacted with a polycarboxylic acid, sulfocarboxylic acid or acid anhydride to introduce an acidic functional group.

A polyol, polycarboxlic acid and acid anhydride employed in Methods [1]-4 and [2]-4 may for example be those similar to the above-mentioned diol (11) and 3- to 8- or higher valent polyol (12), dicarboxylic acid (14) and 3- to 4- or higher valent polycarboxylic acid (14) and acid anhydrides thereof, and the preferred ones are also similar to those listed above. The sulfonic acid group-containing polycarboxylic acid may for example be 4-sulfoisophthalic acid and the like.

The resin (b) may be [1] produced as described later in the specification by using the precursor (b0) of the resin (b) upon producing the composite resin particle or may be [2] produced prior to the production of the composite resin particle.

In addition to the resin (b), an additive (T) (various additives such as filler, colorant, plasticizer, releasing agent, static charge controller, UV absorber, antioxidant, antistatic agent, flame retardant, antibacterial agent, preservative and the like) can be contained in the resin particle (B).

While the amount of the additive (T) may be adjusted as appropriate depending on the respective purpose of use, it is preferably 0.01 to 200% based on the weight of the resin (b). The upper limit of the (T) content is more preferably 150%, especially 100%, while the lower limit is more preferably 0.1%, especially 0.2%.

A method for adding the additive (T) to the resin (b) is not limited particularly, and it is possible, in the method for producing an inventive composite resin particle described later, to admix the additive to an aqueous solution, but it is rather preferable that the resin (a) or resin (b) is mixed previously with (T) and then the mixture is added to and dispersed in an aqueous solvent.

The additive (T) has not necessarily be admixed prior to forming the resin particle (B) and the composite resin particle, and it may be added after forming the resin particle (B) or the composite resin particle. For example, a colorant-free resin particle (B) or composite resin particle is first formed, and then a colorant is added by a known dying method, or the additive (T) can be impregnated together with the solvent (U) and/or plasticizer (V).

When a colorant is added as an additives to the resin particle (B), the colorant may be a colorant which has been treated with a coupling agent (silane coupling agent, titanium coupling agent, aluminum coupling agent and the like).

Especially when the colorant is a carbon black, then it is preferred to be treated with an aluminum coupling agent.

A colorant treated with the coupling agent can be contained in the resin particle (B) for example by preparing a dispersion containing the colorant dispersed with the aid of an aluminum coupling agent followed by mixing the dispersion with the resin (b).

For preparing a dispersion containing a colorant, it is preferable to first conduct a wet mixing of an aluminum coupling agent with a colorant. The mixing of the colorant is accomplished by means of an ordinary mixing and agitating instrument. Typically, for example in a suitable vessel provided with particulate media such as Atrighter, ball mill, sand mill, vibration mill and the like a colorant and an aluminum coupling agent are charged and stirred, and such particulate media may for example be those of steel such as stainless steel and carbon steel as well as alumina, zirconia, silica and the like. Upon this procedure, the temperature in the vessel is kept at 20° C. to 160° C., preferably 20° C. to 100° C., more preferably 30° C. to 60° C. By means of such an agitating instrument, the aggregation of the colorant becomes loose, and the colorant is dispersed until the average particle diameter of the colorant becomes about 0.7 µm or less, preferably about 0.4 µm or less, whereby forcing the aluminum coupling agent to be reacted with and deposited onto the colorant under the agitation load. Then, the colorant dispersion is mixed with a binder resin and the like preferably under a high shear force to ensure re-dispersion for the purpose of avoiding any aggregation of the colorant. The dispersion may be accomplished using a dispersing machine having high shear mechanism of a high speed fin rotation type or a forcible gap passage type such as various homomixers, homogenizers, colloid mills, Ultra-Turrax, Clearmill and the like.

The aluminum coupling agent is not limited particularly as long as it is a compound capable of coupling with a colorant, and may for example be an alkyl (1 to 30 carbon atoms) acetoacetate aluminum isopropylate, aluminum tris (ethyl acetoacetate), aluminum monoisopropoxymonooleoxyethyl acetoacetate and the like.

The amount of the aluminum coupling agent based on 100 parts by weight (hereinafter simply referred to as parts) of a colorant is preferably 0.1 to 100 parts, in view of the dispersion performance of the colorant in the resin (b). The upper limit is more preferably 50 parts, especially 30 parts, while the lower limit is more preferably 0.3 part.

While the resin microparticle (B) can be produced by any non-limiting method, a composite resin particle may be obtained for example by a method described later in the specification which is a production method comprising a step for dispersing the resin (b), the precursor (b0) of the resin (b) or their solution in an aqueous dispersion containing the resin microparticle (A), and then the resin microparticle (A) may be separated from the composite resin particle.

The precursor (b0) of the resin (b) is not limited particularly as long as it is a compound capable of being converted into the rein (b) as a result of a chemical reaction, and may for example be the above-mentioned vinyl monomers (alone or in combination) as well as solutions thereof when the resin (b) is a vinyl resin.

When a vinyl monomer is employed as the precursor (b0), the precursor (b0) can be reacted to yield the resin (b) for example in such a manner that an oil phase comprising an oil-soluble initiator, monomers and, if necessary, the solvent (U) is dispersed and suspended in water in the presence of a water-soluble polymer (T) and then subjected to a radical polymerization with heating (so called suspension polymerization method), or in such a manner that an oil phase comprising monomers and, if necessary, the solvent (U) is emulsified in an aqueous dispersion of the resin microparticle (a) containing an emulsifier and a water-soluble initiator and then subjected to radical polymerization with heating (so called emulsion polymerization method).

The oil-soluble initiator and the water-soluble initiator may be a peroxide initiator (I) and an azo initiator (II). It is also possible to use a combination of a peroxide initiator (I) and a reducing agent as a redox initiator (III). It is also possible to use two or more of (I) to (III) in combination.

(I) Peroxide initiators which may be employed are oil-soluble peroxide initiators (I-1) and water soluble peroxide initiators (I-2).

(I-1) The oil-soluble peroxide initiator may for example be acetylcyclohexylsulfonyl peroxide, isobutyryl peroxide, diisopropyl peroxydicarbonate, di-2-ethylhexyl peroxydicarbonate, 2,4-dichlorobenzoyl peroxide, t-butyl peroxypivalate, 3,5,5-trimethylhexanonyl peroxide, octanoyl peroxide, decanoyl peroxide, lauroyl peroxide, stearoyl peroxide, propionitrile peroxide, succinic acid peroxide, acetyl peroxide, t-butylperoxy-2-ethyl hexanoate, benzoyl peroxide, p-chlorobenzoyl peroxide, t-butyl peroxyisobutyrate, t-butyl peroxymaleic acid, t-butyl peroxylaurate, cyclohexanone peroxide, t-butyl peroxyisopropyl carbonate, 2,5-dimethyl-2,5-dibenzoyl peroxyhexane, t-butylperoxyacetate, t-butyl peroxybenzoate, diisobutyl diperoxyphthalate, methyl ethyl ketone peroxide, dicumyl peroxide, 2,5-dimethyl-2,5-di-t-butyl peroxyhexane, t-butylcumyl peroxide, t-butyl hydroperoxide, di-t-butyl peroxide, diisopropylbenzene hydroperoxide, p-menthane hydroperoxide, pinane hydroperoxide, 2,5-dimethylhexane-2,5-dihydroperoxide, cumene peroxide and the like.

(I-2) The water-soluble peroxide initiator may for example be hydrogen peroxide, peracetic acid, ammonium persulfate, potassium persulfate, sodium persulfate and the like.

(II) The azo initiator may be an oil-soluble azo initiator (II-1), a water-soluble azo initiator (II-2) and the like.

(II-1) The oil-soluble azo initiator may for example be 2,2'-azobisisobutyronitrile, 1,1'-azobiscyclohexane 1-carbonitrilenitrile, 2,2'-azobis-4-methoxy-2,4-dimethylvaleronitrile, 2,2'-azobis-2,4-dimethylvaleronitrile, dimethyl-2,2'-azobis(2-methylpropionate), 1,1'-azobis(l-acetoxy-1-phenylethane) and 2,2'-azobis(4-mehtoxy-2,4-dimethylvaleronitrile) and the like.

(II-2) The water-soluble azo initiator may for example be azobisamidinopropanoate, azobiscyanovaleric acid (salt), 2,2'-azobis[2-methyl-N-(2-hydroxyethyl)propionamide] and the like.

(III) The redox initiator may be an oil-soluble redox initiator (III-1), water-soluble redox initiator (III-2) and the like.

(III-1) The oil-soluble redox initiator may for example be a combination of an oil-soluble peroxide such as a hydroperoxide (t-butylhydroxy peroxide, cumene hydroxyperoxide and the like), dialkyl peroxide(lauroyl peroxide and the like) and diacyl peroxide (benzoyl peroxide and the like) and the like with an oil-soluble reducing agent such as tertiary amine (triethylamine, tributylamine and the like), naphthate, mercaptane (mercaptoethanol, laurylmercaptan and the like), organometal compound (triethylalluminium, triethylborone, diethylzinc and the like) and the like.

(III-2) The water-soluble redox initiator may for example be a combination of a water-soluble peroxide such as a persulfate (potassium persulfate, ammonium persulfate and the like), hydrogen peroxide and hydroperoxide (t-butylhydroxy peroxide, cumene hydroxyperoxide and the like) with a water soluble inorganic or organic reducing agent (divalent iron salt, sodium hydrogen sulfite, alcohol, dimethylaniline and the like).

When the resin (b) is a polyurethane, epoxy resin, polyester resin and the like, the precursor (b0) may be a combination of a reactive group-containing prepolymer (α) with a curing agent (β) discussed later in the specification.

As used herein, the term "reactive group" means a group capable of reacting with a curing agent (β).

In such a case, the precursor (b0) can be reacted to yield a resin particle (B) by any of the following methods [1] to [3].

[1] A method in which an oil phase containing reactive group-containing prepolymer (α), the curing agent (β) and, if necessary, the solvent (U) is dispersed in an aqueous dispersion of the resin microparticle (A), and the reactive group-containing prepolymer (α) and the curing agent (β) are reacted by heating to form the resin particle (B) comprising the resin (b) at the same time with the formation of the composite resin particle comprising the resin particle (B) and the resin microparticle (A).

[2] A method in which the reactive group-containing prepolymer (α) or its solution is dispersed in an aqueous dispersion of the resin microparticle (A), to which the water-soluble curing agent (β) is added to effect a reaction to form the resin particle (B) comprising a resin (b) at the same time with the formation of a composite resin particle comprising the resin particle (B) and the resin microparticle (A).

[3] A method, in the case of the reactive group-containing prepolymer (α) capable of being cured when reacted with water, in which the reactive group-containing prepolymer (α) or its solution is dispersed in an aqueous dispersion of the resin microparticle (A) whereby effecting a reaction with water to form the resin particle (B) comprising the resin (b) at the same time with the formation of the composite resin particle comprising the resin particle (B) and the resin microparticle (A).

The combination of a reactive group possessed by the reactive group-containing prepolymer (α) and the curing agent (β) may for example be any of the following combinations [1] and [2].

Combination [1]: A combination of the reactive group-containing prepolymer (α1) having a reactive functional group capable of reacting with an active hydrogen-containing group and with an active hydrogen-containing compound (β1).

Combination [2]: A combination of the reactive group-containing prepolymer (α2) having an active hydrogen-containing group with the curing agent (β2) having a functional group capable of reacting with the active hydrogen-containing group.

Among those listed above, the combination [1] is preferred in view of the reaction rate in water.

The functional group capable of reacting with an active hydrogen-containing group may for example be an isocyanate group, blocked isocyanate group, epoxy group, acid anhydride-derived group, acid halide (acid chloride, acid bromide and the like)-derived group and the like.

Among those listed above, an isocyanate group, blocked isocyanate group and epoxy group are preferred, with an isocyanate group and blocked isocyanate group being more preferred.

The blocked isocyanate group means an isocyanate group which is blocked by a blocking agent.

The blocking agent may for example be a known blocking agent, such as an oxime [acetoxime, methylisobutyl ketoxime, diethyl ketoxime, cyclopentanoneoxime, cyclohexanoneoxime, methylethyl ketoxime and the like]; lactam [γ-butyrolactam, ε-caprolactam, γ-valerolactam and the like]; aliphatic alcohol of 1 to 20 carbon atoms [ethanol, methanol, octanol and the like]; phenol [phenol, m-cresol, xylenol, nonylphenol and the like]; active methylene compound [acetylacetone, ethyl malonate, ethyl acetoacetate and the like]; basic nitrogen-containing compound [N,N-diethylhydroxylamine, 2-hydroxypyridine, pyridine N-oxide, 2-mercaptopyridine and the like]; and mixtures of two or more of those listed above.

Among those listed above, an oxime is preferred, with methylethyl ketoxime being more preferred.

The backbone of the reactive group-containing prepolymer (α) may be a polyether, polyester, epoxy resin, polyurethane and the like.

Among those listed above, a polyester, epoxy resin and polyurethane are preferred, with a polyester and polyurethane being more preferred.

The polyether may for example be a polyethylene oxide, polypropylene oxide, polybutylene oxide, polytetramethylene oxide and the like.

The polyester may for example be a polycondensate of the diol (11) with the dicarboxylic acid (13), polylactone (ring-opening polymerization product of ε-caprolactone and the like) and the like.

The epoxy resin may for example be an addition condensate of a bisphenol (bisphenol A, bisphenol F, bisphenol S and the like) with epichlorohydrin and the like.

The polyurethane may for example be a polyaddition product of the diol (11) with the polyisocyanate (15), polyaddition product of a polyester with the polyisocyanate (15) and the like.

A method by which a reactive group is contained in a polyester, epoxy rein or polyurethane is not limited particularly, and one exemplified is any of the following methods [1] and [2].

[1] A method in which one of the constituents of a polyester, epoxy resin or polyurethane is employed in an excessive amount whereby allowing the reactive groups in the constituent to remain.

[2] A method in which one of the constituents of a polyester, epoxy resin or polyurethane is employed in an excessive amount whereby allowing the functional groups in the constituent to remain, and the a compound containing a functional group (reactive group) capable of reacting with the remaining functional groups is then reacted.

Method [1] yields a hydroxyl group-containing polyester prepolymer, carboxyl group-containing polyester prepolymer, acid halide-derived group-containing polyester prepolymer, hydroxy group-containing epoxy resin prepolymer, epoxy group-containing epoxy resin prepolymer, hydroxyl group-containing polyurethane prepolymer, isocyanate group-containing polyurethane prepolymer and the like.

In Method [1], the ratio between respective constituents for example in the case of the hydroxyl group-containing polyester prepolymer may for example be so adjusted that the ratio between an alcohol component (diol (11), polyol (12) and the like) and a carboxylic acid component (dicarboxylic acid (13), polycarboxylic acid (14) and the like) can preferably be represented as the equivalent ratio between the hydroxyl group [OH] and the carboxyl group [COOH], i.e., [OH]/[COOH] to be 8/1 to 1/1, more preferably 2/1 to 1/1, especially 1.3/1 to 1.02/1.

Also in the cases of a carboxyl group-containing polyester prepolymer, acid halide-derived group-containing polyester prepolymer, hydroxyl group-containing polyurethane prepolymer, isocyanate group-containing polyurethane prepolymer and the like, the preferred ratio is similar although the composition of the constituents is changed.

In Method [2], a prepolymer obtained in Method [1] is reacted with a polyisocyanate to yield an isocyanate group-containing prepolymer, reacted with a blocked polyisocyanate to yield a blocked isocyanate group-containing prepolymer, reacted with a polyepoxide to yield an epoxy group-containing prepolymer, reacted with a compound having two or more acid anhydride-derived groups to yield an acid anhydride-derived group-containing prepolymer.

In Method [2], the amount of a compound having a reactive group for example in the case where the hydroxy group-containing polyester is reacted with a polyisocyanate to give an isocyanate group-containing polyester prepolymer may for example be so adjusted that the ratio between the hydroxyl group-containing polyester and the polyisocyanate can preferably be represented as the equivalent ratio between the isocyanate group [NCO] and the hydroxyl group [OH], i.e., [NCO]/[OH] to be 5/1 to 1/1, more preferably 4/1 to 1.2/1, especially 2.5/1 to 1.5/1.

Also in the cases of other prepolymers, the preferred ratio is similar although the composition of the constituents is changed.

The average number of reactive groups per molecule of the reactive group-containing prepolymer (α) is preferably 1 to 3, more preferably 1.5 to 3, especially 1.8 to 2.5. Within this range, the mechanical strength of a resin obtained by a reaction with the curing agent (β) can readily be increased.

The Mn of the reactive group-containing prepolymer (α) is preferably 500 to 30,000. The upper limit of the Mn is more preferably 20,000, especially 10,000, while the lower limit is more preferably 1,000, especially 2,000.

The Mw of the reactive group-containing prepolymer (α) is preferably 1,000 to 50,000. The upper limit of the Mw is more preferably 40,000, especially 20,000, while the lower limit is more preferably 2,000, especially 4,000.

The viscosity of the reactive group-containing prepolymer (α) at 100° C. is preferably 50 to 50,000 MPa·S. The upper limit of the viscosity is more preferably 5,000 MPa·S, especially 3,000 MPa·S, while the lower limit is more preferably 100 MPa·S, especially 150 MPa·S. Within this range, a composite resin particle having a sharp particle size distribution in a spindle shape can readily be obtained.

As the active hydrogen-containing compound (β1) may for example be the above-exemplified water, diol (11), 3- to 6- or higher valent polyol (12), dicarboxylic acid (13), 3- to 4- or higher valent polycarboxylic acid (14), polyamine (16) and polythiol (17), as well as those which have been converted into a blocked form using a removable compound, including a polyamine which has been converted into a blocked form using a removable compound, polyol which has been converted into a blocked form using a removable compound and the like.

The polyamine which has been converted into a blocked form using a removable compound may for example be a ketimine compound obtained by a dehydration reaction between a polyamine (16) and a ketone of 3 to 8 carbon atoms (for example, acetone, methyl ethyl ketone, methyl isobutyl ketone and the like), an aldimine compound obtained by a dehydration reaction between the polyamine (16) and an aldehyde compound of 1 to 8 carbon atoms (for example, formaldehyde, acetaldehyde and the like), as well as an enamine compound or oxazolidine compound consisting of the polyamine (16) and a ketone of 3 to 8 carbon atoms or an aldehyde of 2 to 8 carbon atoms and the like.

Among those listed above, an optionally blocked polyamine, optionally blocked polyol and water are preferred, with an optionally blocked polyamine and water being more preferred and a polyamine, ketimine compound and water being especially preferred, and those employed most preferably are 4,4'-diaminodiphenylmethane, xylylene diamine, isophorone diamine, ethylene diamine, diethylene triamine, triethylene tetramine and ketimine compounds obtained therefrom with ketones, as well as water.

Upon producing the resin particle (B) (upon producing the composite resin particle), a reaction terminator (βs) can be employed if necessary together with the active hydrogen-containing compound (β1). By using the reaction terminator together with (β1) in a certain ratio, the molecular weight of the resin (b) as a constituent of the resin particle (B) can readily be adjusted.

The reaction terminator (βs) may for example be a primary or secondary monoamine of 1 to 40 carbon atoms (diethylamine, dibutylamine, butylamine, laurylamine, monoethanolamine, diethanolamine and the like); a blocked monoamine of 3 to 40 carbon atoms (ketimine compound and the like); monool of 1 to 40 carbon atoms (methanol, ethanol, isopropanol, butanol, phenol and the like); monomercaptan of 2 to 40 carbon atoms (butylmercaptan, laurylmercaptane and the like); monoisocyanate of 5 to 40 carbon atoms (butyl isocyanate, lauryl isocyanate, phenyl isocyanate and the like); monoepoxide of 2 to 40 carbon atoms (butylglycidyl ether and the like) and the like.

In the above-mentioned combination [2] (combination the reactive group-containing prepolymer (α2) having the active hydrogen-containing group with the curing agent (β2) having a functional group capable of reacting with the active hydrogen-containing group), the active hydrogen-containing group possessed by the reactive group-containing prepolymer (α) may for example be an amino group, hydroxyl group (alcoholic hydroxyl group and phenolic hydroxyl group), mercapto group, carboxyl group as well as blocked organic groups derivatized therefrom with removable compounds (ketones, aldehydes and the like) (ketimine-containing group, aldimine-containing group, oxazolidine-containing group, enamine-containing group, acetal-containing group, ketal-containing group, thioacetal-containing group, thioketal-containing group and the like) and the like.

Among those listed above, an amino group, hydroxyl group or a blocked organic group derivatized therefrom with a removable compound are preferred, with a hydroxyl group being more preferred.

The curing agent (β2) having a functional group capable of reacting with the active hydrogen-containing group may for example be the polyisocyanate (15), polyepoxide (18), dicarboxylic acid (13), polycarboxylic acid (14), compound having two or more acid anhydride-derivatized groups, compound having two or more acid halide-derivatized groups and the like.

Among those listed above, a polyisocyanate and polyepoxide are preferred, with a polyisocyanate being more preferred.

The compound having two or more acid anhydride-derivatized groups may for example be pyromellitic anhydride, maleic anhydride (co)polymer and the like.

The compound having two or more acid halide-derivatized groups may for example be an acid halide of the dicarboxylic acid (13) or polycarboxylic acid (14) (acid chloride, acid bromide, acid iodide and the like).

Upon producing the resin particle (B) (upon producing the composite resin particle), the reaction terminator (βs) can be employed if necessary together with the curing agent (β2) having a functional group capable of reacting with the active hydrogen-containing group. By using a reaction terminator together with (β2) in a certain ratio, the molecular weight of the resin (b) as a constituent of the resin particle (B) can readily be adjusted.

The amount of the curing agent (β) employed when represented as the ratio between the reactive group equivalent [α] in the reactive group-containing prepolymer (α) and the active hydrogen-containing group equivalent in the curing agent (β), i.e., [α]/[β], is preferably 1/2 to 2/1, more preferably 1.5/1 to 1/1.5, especially 1.2/1 to 1/1.2.

When the curing agent (β) is water, then water is handled as a divalent active hydrogen-containing group-containing compound.

The Mw of the resin (b) resulting from the reaction of the reactive group-containing prepolymer (α) with the curing agent (β) is preferably 3,000 or higher. The upper limit of the Mw is more preferably 10,000,000, especially 1,000,000, while the lower limit is preferably 3,000, especially 5,000.

It is also possible to allow a polymer which does not react with the reactive group-containing prepolymer (α) or the curing agent (β) [so called a dead polymer] to be contained in the reaction system upon reaction of the reactive group-containing prepolymer (α) with the curing agent (β).

In such a case, the resin (b) is a mixture of a resin obtained by the reaction of the reactive group-containing prepolymer (α) with the curing agent (β) and the dead polymer.

While the time of the reaction of the reactive group-containing prepolymer (α) with the curing agent (β) may appropriately be selected depending on the reactivity of the combination of the type of the reactive group possessed by the prepolymer (α) and the curing agent (β), it is preferably 10 minutes to 40 hours, more preferably 30 minutes to 24 hours, especially 30 minutes to 8 hours.

The temperature of such a reaction is preferably 0 to 150° C., more preferably 50 to 120° C.

If necessary, a known catalyst can also be employed. Typically, a reaction of an isocyanate with an active hydrogen compound employs dibutyltin dilaurate, dioctyltin dilaurate and the like.

While a method for producing the composite resin particle according to the present invention is not limited particularly, a preferred typical method is a production method comprising the steps in which the resin (b) constituting (B), the precursor (b0) of (b) and/or a solution thereof are dispersed in an aqueous dispersion containing (A) and if (b0) or a solution thereof is employed then (b0) is further reacted to form (B) comprising (b) in the aqueous dispersion of (A) whereby forming the composite resin particle as (B) on the surface of which (A) has been deposited.

After an aqueous dispersion of the composite resin particle obtained by the above-mentioned production method is subjected for example to a solid/liquid separation (with repeating the solid/liquid separation if necessary with adding water and the like) followed by drying to remove an aqueous solvent, an inventive composite resin particle can be obtained.

A dispersing machine and/or a shearing machine employed in a method described above may be any commercially available emulsifier and/or disperser, including a batch emulsifier such as a homogenizer (produced by IKA), polytron (produced by Kinematica), TK autohomomixer (produced by TOKUSHU KIKAI KOGYO), ultradisperser (produced by Yamato Scientific Co., Ltd.) and the like; continuous emulsifier such as EBARA milder (produced by EBARA SEISAKUSHO), TK Filmics, TK pipeline homomixer (produced by TOKUSHU KIKAI KOGYO), colloid mill (produced by SHINKO Pantec Co., Ltd.), slasher, trigonal wet microgrinder (produced by MITSUIMIIKE KAGAKU KOGYO), Cavitron (produced by Eurotec Ltd.) and fine flow mill (produced by TAIHEIYO KIKO) and the like; high pressure emulsifier such as a microfluidizer (produced by MIZUHO KOGYO), nanomizer (produced by NANOMIZER), APV Gaulin (produced by Gaulin) and the like; membrane emulsifier such as a membrane emulsifier (produced by REIKA KOGYO); vibration emulsifier such as Vibromixer (produced by Reica Co.,); as well as ultrasonic emulsified such as an ultrasonic homogenizer (produced by Brason) and the like.

Among those listed above, those preferred in view of the uniformity of the particle diameter are an APV Gaulin, homogenizer, TK autohomomixer, EBARA milder, ultradisperser, TK Filmics and TK pipeline homomixer, those more preferred are TK autohomomixer, EBARA milder, TK Filmics and TK pipeline homomixer, and those more preferred especially are TK autohomomixer, TK Filmics and TK pipeline homomixer.

The composite resin particle of the first aspect of the present invention is obtained by subjecting an aqueous dispersion to a high shear force upon dispersing if the resin (b) and/or the precursor (b0) is employed, and upon dispersing and if necessary upon removing the solvent if a solution of (b) and/or (b0) is employed. By means of subjecting to a high shear force, the (SF-1) of a composite resin particle readily becomes within the range specified in the first aspect of the invention, resulting in a resin particle whose powder flawability and viscosity profile when used as an additive are excellent.

For obtaining the composite resin particle of the first aspect of the invention while using a high shear force, then those to be employed among the above-mentioned instruments are a batch emulsifier, continuous emulsifier and high pressure emulsifier, which are operated preferably under the following conditions.

When being subjected to a high shear force, an aqueous dispersion in the shearing step has a viscosity at that temperature which is preferably 5 to 100,000 mPa·s, more preferably 10 to 60,000 mPa·s, especially 15 to 40,000 mPa·s. A viscosity of the aqueous dispersion within this range allows the time for deforming the shape of a resin particle under a high shear force to be reduced, and makes it difficult after the deformation to recover a spherical shape, resulting in a dispersion whose shape after the deformation is stable.

While the temperature at which a high shear force is exerted is not limited particularly, it is preferably 0 to 150° C., more preferably 5 to 98° C., especially 10 to 80° C. in order to promote the deformation of the resin particle and to prevent the adhesion of the resin particles.

The shear force may vary depending on the viscosity of an aqueous dispersion (at the shearing temperature), the time during which the shear force is exerted and the temperature at that time, and may appropriately be selected, and, for the purpose of promoting the deformation of the resin particle and promoting the control of the particle size distribution, the above-exemplified shear force-exerting instrument is used, for example [1] when the viscosity of the aqueous dispersion is 1 to 200 mPa·s, to exert a shear force preferably at 500 to 50,000 rpm, more preferably at 2,000 to 30,000 rpm, especially at 4,000 to 20,000 rpm. [2] When the viscosity of the aqueous dispersion is 200 to 40,000 mPa·s, it is preferable to exert a shear force preferably at 200 to 40,000 rpm, more preferably at 500 to 30,000 rpm, especially at 1,000 to 20,000 rpm. [3] When the viscosity of the aqueous dispersion is 40,000 to 100,000 mPa·s, it is preferable to exert a shear force preferably at 50 to 30,000 rpm, more preferably at 100 to 25,000 rpm, especially at 500 to 20,000 rpm.

The time during which a shear force is exerted may vary depending on the instrument used for exerting the shear force and is not limited particularly, and it is preferably 15 minutes to 24 hours, more preferably 20 minutes to 20 hours, especially 25 minutes to 12 hours, most preferably 30 minutes to 8 hours for example when a batch emulsifier is employed as an instrument for exerting a high shear force. When a continuous emulsifier is employed, the time is preferably 0.1 second to 20 hours, more preferably 1 second to 10 hours, especially 3 seconds to 8 hours, most preferably 5 seconds to 5 hours. When a high pressure emulsifier is employed, the time is preferably 0.01 second to 10 hours, more preferably 0.1 second to 8 hours, especially 0.5 second to 5 hours, most preferably 1 second to 3 hours.

In a production method described above, the weight ratio of the resin (a), resin (b) and precursor (b0) are so adjusted that the value of (A)/(B) is within the range specified above.

The amount of an aqueous solvent employed per 100 parts of the resin (b) and/or precursor (b0) is preferably 50 to 2,000 parts. The upper limit is more preferably 1000 parts, especially 500 parts, while the lower limit is more preferably 100 parts. An amount below this range may lead to a poor dispersion state of (b), while an amount exceeding this range may lead to an economical disadvantage.

The amount of an aqueous solvent per 100 parts of the resin (a) is preferably 50 to 2,000 parts. The upper limit is more preferably 1000 parts, especially 500 parts, while the lower limit is more preferably 100 parts. An amount below this range may lead to a poor dispersion state of (a), while an amount exceeding this range may lead to an economical disadvantage.

Any liquid whose essential constituent is water can be employed as an aqueous solvent without limitation, and it is possible to use water, aqueous solution of a solvent, aqueous solution of the surfactant (S), aqueous solution of the water-soluble polymer (T), as well as mixtures thereof.

A solvent may for example be, among the solvents (U) described above, an ester solvent, ester ether solvent, ether solvent, ketone solvent, alcohol solvent, amide solvent, sulfoxide solvent, heterocyclic compound solvent, as well as a mixture of two or more of these solvents.

When a solvent is contained, the amount of the solvent is preferably 1 to 80% based on the weight of an aqueous solvent. The upper limit is preferably 80%, more preferably 70%, especially 30%, while the lower limit is more preferably 2%, especially 5%.

When the surfactant (S) is employed, the amount is preferably 0.001 to 0.3% based on the weight of an aqueous solvent. The upper limit is more preferably 0.2%, especially 0.15%, while the lower limit is more preferably 0.005%, especially 0.01%.

When the water-soluble polymer (T) is employed, the amount is preferably 0.0001 to 0.2% based on the weight of an aqueous solvent. The upper limit is more preferably 0.15%, especially 0.1%, while the lower limit is more preferably 0.0002%, especially 0.0005%.

The volume average particle diameter (DC) of the composite resin particle can be adjusted as desired by adjusting the volume average particle diameter (DA) of the resin microparticle (A) appropriately. For example, when a composite resin particle having a value of (DC) of 1 μm or less, the value of (DA) is preferably 0.0005 to 0.4 μm, more preferably 0.001 to 0.3 μm. When a composite resin particle having a value of (DC) of 1 to 10 μm, the value of (DA) is preferably 0.001 to 3 μm, more preferably 0.03 to 2 μm. When a composite resin particle having a value of (DC) of 10 μm or more, the value of (DA) is preferably 0.005 to 4 μm, more preferably 0.05 to 3 μm.

When dispersing the resin (b) and/or the precursor (b0) in an aqueous dispersion of the resin microparticle (A), it is preferred that the (b) and the (b0) are liquid. When the resins (b) and (b0) are solid at ambient temperature, they may be dispersed as liquids at an elevated temperature higher than the melting points, or the solutions of the (b) or (b0) may also be employed.

The viscosity of the resin (b), precursor (b0) of the resin (b) or its solution is preferably 10 to 50,000 mPa·s in view of the particle diameter uniformity. The upper limit of the viscosity is more preferably 30,000 mPa·s, especially 20,000 mPa·s, while the lower limit is more preferably 100 mPa·s, especially 200 mPa·s.

A viscosity is measured with 30 rotations at the temperature at which the dispersion is formed using a rotor type viscometer (for example, BL viscometer, BM viscometer, BH viscometer, TOKYO KEIKI).

Upon dispersing, the temperature is preferably 0 to 150° C., more preferably 5 to 98° C., especially 10 to 60° C. When the temperature exceeds 100° C., it is a temperature under pressure. In the case of a high viscosity of a dispersion, it is preferable to raise the temperature to reduce the viscosity to a level within the preferable range specified above prior to effecting emulsification or dispersion.

A solvent employed for the solution of a resin (b) or a solution of the precursor (b0) is not limited particularly as long as it is a solvent in which the resin (b) can be dissolved at ambient temperature or with heating, and may for example be similar to the solvent (U). Among those listed above, one preferred is a solvent having a difference of 3 or less in the SP value from (b) or (b0), although it may vary depending on the types of the resin (b) and the precursor (b0), and one more preferred in view of the particle diameter uniformity of a composite resin particle is a solvent which can dissolve the resin (b) [the amount dissolved in 100 g of the solvent is preferably 5 g or more, more preferably 10 g or more] but which hardly dissolves or swells the resin microparticle (A) comprising the resin (a) [the amount dissolved in 100 g of the solvent is preferably 10 g or less, more preferably 5 g or less].

The concentration of a resin when using a solvent may be adjusted so that the viscosity of the solution at the temperature upon dispersing is within the above-mentioned appropriate range, and is preferably 5 to 95%, more preferably 10 to 90%, especially 20 to 80%.

A method described above can employ an emulsifier, dispersing agent and the like, and such emulsifier and dispersing agent may be any known surfactant (S), water-soluble polymer (T) and the like. It is also possible to use the solvent (U), plasticizer (V) and the like as an auxiliary agent for the emulsification and dispersion.

For the purpose of enhancing the adhesive performance of the resin microparticle (A) and the resin particle (B) in the composite resin particle, it is effective, upon dispersing in an aqueous dispersion, that the resin microparticle (A) and the resin particle (B) are charged oppositely, that when the resin microparticle (A) and the resin particle (B) are charged identically then among the surfactant (S) and the water-soluble polymer (T) one charged oppositely to the resin microparticle (A) and the resin particle (B) is employed, and that the difference in the SP value between the resin (a) and the resin (b) is limited to 2 or less. A higher adhesive performance is more preferable since the value of (TA)/(TC) becomes higher.

An aqueous solvent can be removed by any of the following Methods [1] to [3] as well as combinations thereof.

[1] A method in which an aqueous dispersion is dried under reduced pressure or atmospheric pressure.

[2] A method in which a solid/liquid separation is conducted using a centrifuge, Sparkler filter and/or filter press to obtain a solid which is then dried.

[3] A method in which an aqueous dispersion is frozen and dried (so called lyophilization).

In Methods [1] and [2] described above, a drier may be any known equipment such as a fluidized bed drier, reduced pressure drier, circulatory blower drier, air flow drier and the like.

If necessary, a wind velocity sieving machine or a mesh is employed to sieve particles to obtain a desired particle size distribution.

It is possible to impart the surface of a resin particle (B) with a smooth surface or a desired roughness by means of changing the particle diameter ratio (DA/DB) between the resin microparticle (A) and the resin particle (B), the ratio (TA/TC), the depth to which the resin microparticle (A) is embedded into the resin particle (B), and the like.

The ratio (TA/TC) and the depth to which the resin microparticle (A) is embedded into the resin particle (B) can be controlled by the methods described below.

[1] By allowing the resin microparticle (A) and the resin particle (B) to be charged oppositely, the value (TA/TC) and the depth are increased. In such a case, this tendency becomes more marked by increasing the charge in each of the resin microparticle (A) and the resin particle (B).

[2] By allowing the resin microparticle (A) and the resin particle (B) to be charged at an identical polarity (both positive or both negative), the value (TA/TC) and the depth tend to be reduced. In such a case, the value (TA/TC) becomes higher generally by using the surfactant (S) and/or the water-soluble polymer (T) [especially one charged oppositely to the resin microparticle (A) and the resin particle (B)]. When using the water-soluble polymer (T), then a larger molecular weight of the water-soluble polymer (T) gives a greater depth.

[3] When the resin (a) is a resin having an acidic functional group such as a carboxyl group, phosphono group, sulfo group and the like (generally, one having a molecular weight per acidic functional group of 1,000 or less is preferred), a lower pH of an aqueous solvent gives a greater (TA/TC) and greater depth. On the contrary, a higher pH gives a lower (TA/TC) and smaller depth.

[4] When the resin (a) is a resin having a basic functional group such as a primary amino group, secondary amino group, tertiary amino group, quaternary ammonium salt-derived group and the like (generally, one having a molecular weight per basic functional group of 1,000 or less is preferred), a higher pH of an aqueous solvent gives a greater (TA/TC) and greater depth. On the contrary, a lower pH gives a lower (TA/TC) and smaller depth.

[5] A smaller difference in the SP value between the resin (a) and the resin (b) gives a greater (TA/TC) and a greater depth.

For improving the powder flawability of the resin particle (B), the BET specific surface area of the resin particle (B) is preferably 0.5 to 9 $m^2/g$, especially 0.7 to 8 $m^2/g$.

The BET specific surface area can be determined (measurement gas: He/Kr=99.9/0.1 vol %, quantification gas: nitrogen) using a specific surface area meter (for example, trade name: QUANTASORB, Yuasa-Ionics company, Limited).

Similarly in view of the powder flowability, the surface average center line roughness (Ra) of a resin (B) is preferably 0.01 to 0.8 µm, especially 0.1 to 0.7 µm.

A value of (Ra) means a value of an arithmetic mean of the absolute value of the deviation between the roughness curve and its center line, and can be measured for example by a scanning probe microscope system (for example, one produced by TOYO TECHNICA Corporation).

The resin particle (B) can be obtained for example by [1] a method in which in an aqueous dispersion containing the composite particle the resin microparticle (A) and the resin particle (B) which are adhering to each other are cleaved and then the resin microparticle (A) is separated from said aqueous dispersion, or by [2] a method in which in said aqueous dispersion the resin microparticle (A) is dissolved or melted without dissolving or melting the resin particle (B) and then the solution or molten mass of the resin microparticle (A) is separated as desired.

By removing an aqueous solvent from an aqueous dispersion from which the resin microparticle (A) has been removed, the resin particle (B) is obtained. A method for removing the aqueous solvent may for example be a method similar to that employed for a composite resin particle.

A method for cleaving the resin microparticle (A) and the resin particle (B) which are adhering to each other may for example be [1] a method in which an aqueous dispersion is treated ultrasonically; [2] a method in which an aqueous dispersion is subjected to a 1.5- to 100-fold dilution with water and/or an aqueous solvent (for example, methanol, ethanol, acetone and the like) and subjected to a shear force by stirring; [3] a method in which an aqueous dispersion is combined with an acid, alkali or inorganic salt (sodium chloride, sodium carbonate, sodium hydrogen carbonate and the like) and the like and subjected to a shear force by stirring; [4] a method in which an aqueous dispersion is heated and subjected to a shear force by stirring; and [5] a method in which a solvent is removed in the case that an aqueous dispersion contains a solvent [for example when a solution of the resin (a) and/or a solution of the resin (b) is dispersed in an aqueous solvent or when a solvent is dispersed or dissolved in an aqueous solution].

A method for dissolving or melting the resin microparticle (A) may for example be [1] a method in which when the resin (a) is a resin having an acidic functional group such as a carboxyl group, phosphono group, sulfo group and the like (generally, one having a molecular weight per acidic functional group of 1,000 or less is preferred) then the aqueous dispersion is supplemented with an alkali (equimolar amount or more) such as sodium hydroxide, potassium hydroxide, ammonia, DBU and the like or its aqueous solution, [2] a method when the resin (a) is a resin having a basic functional group such as a primary amino group, secondary amino group, tertiary amino group, quaternary ammonium salt-derived group and the like (generally, one having a molecular weight per basic functional group of 1,000 or less is preferred) then the aqueous dispersion is supplemented with an acid (equimolar amount or more) such as hydrochloric acid, sulfuric acid, phosphoric acid, acetic acid and the like or its aqueous solution; [3] a method in which when the resin (a) is soluble in the solvent (U) {generally, it is preferable that the difference in the SP value between the resin (a) and the solvent (U) is 2.5 or less} then the aqueous dispersion is supplemented with a certain solvent (U); as well as a method employing a heating at a temperature at which the resin particle (B) is not melted but the resin microparticle (A) is melted.

A method for separating the resin microparticle (A), its solution or molten mass thereof may for example be [1] a method employing a filtration through a filter paper, filter pad or mesh having a certain pore size to remove only the resin particle (B); and [2] a method in which the resin particle (B) is precipitated exclusively by a centrifugation and the resin microparticle (A), its solution or molten mass contained in the supernatant is removed.

The resin particle (B) thus obtained has a shape factor (SF-1) which is similar to that of a composite resin particle before removal of the resin microparticle (A). For example, from a composite resin particle of the first aspect of the invention having an (SF-1) of 115 to 800 the resin particle (B) having an (SF-1) of 115 to 800 is obtained.

The composite resin particle and the resin particle (B) according to the present invention is very suitable as an additive in a paint or coating, a powder coating, a cosmetic additive, a slush molding resin, an electronic part assembly spacer for example for a liquid crystal display, an electric measurement device standard particle, a toner for an electrophotography, electrostatic recording and electrostatic printing, a hot melt adhesive as well as other molding materials.

EXAMPLES

The present invention is further described in the following EXAMPLES which are not intended to restrict the present invention.

Production Example 1

A reaction vessel fitted with a stirrer and a thermometer was charged with 47 parts of styrenated phenol EO adduct (Eleminol HB-12, SANYO KASEI KOGYO) and 232 parts of bisphenol A diglycidyl ether (Epikote 828, YUKA SHELL), which were dissolved uniformly.

Then, water was added dropwise to the reaction vessel with stirring. Upon adding 31 parts of water, the inside of the reaction vessel was emulsified and became milky white. After a further dropwise addition of 224 parts of water, an emulsion (1) was obtained.

This emulsion (1) was heated to 70° C., and treated dropwise with a mixture of 20 parts of ethylene diamine and 446 parts of water over a period of 2 hours while keeping the temperature at 70° C.

After completion of the dropwise addition, the reaction and the maturing were ensured at 70° C. for 5 hours followed by 90° C. for 5 hours, whereby obtaining an amine-cured epoxy resin aqueous dispersion [resin microparticle (A1) dispersion].

The [resin microparticle (A1) dispersion] was observed by a laser particle size distribution analyzer LA-920 (HORIBA, Ltd.), and the volume average particle diameter of (A1) was revealed to be 0.80 μm.

A part of the [resin microparticle (A1) dispersion] was centrifuged and combined with water prior to a further centrifugation which was repeated twice, and then dried to isolate a resin portion {resin microparticle (A1)}. The Tg (measured by DSC, hereinafter the same applies to Tg) was 122° C.

Production Example 2

A reaction vessel fitted with a stirrer and a thermometer was charged with 683 parts of water, 11 parts of methacrylic acid EO adduct sulfate sodium salt (Eleminol RS-30, SANYO KASEI KOGYO), 139 parts of styrene, 138 parts of methacrylic acid and 1 part of ammonium persulfate, which were stirred at 400 rpm for 15 minutes to obtain a white emulsion.

This emulsion was heated to 75° C. and reacted for 5 hours. Then 30 parts of a 1% aqueous solution of ammonium persulfate was added, and the mixture was matured at 75° C. for 5 hours to obtain an aqueous dispersion [resin microparticle (A2) dispersion] of a vinyl resin (styrene-methacrylic acid-methacrylic acid EO adduct sulfate sodium salt copolymer).

The [resin microparticle (A2) dispersion] was observed by an LA-920, which revealed the volume average particle diameter of (A2) was 0.12 μm.

A part of the [resin microparticle (A2) dispersion] was dried to isolate a resin portion {resin microparticle (A2)}. The Tg of (A2) was 155° C.

Production Example 3

A reaction vessel fitted with a condenser, stirrer and nitrogen inlet was charged with 343 parts of bisphenol A EO 2-mole adduct, 166 parts of isophthalic acid and 2 parts of dibutyltin oxide, and the reaction was conducted under atmospheric pressure at 230° C. for 8 hours, followed by the reaction for 5 hours under reduced pressure of 10 to 15 mmHg, and then the mixture was cooled to 110° C., combined with 17 parts of isophorone diisocyanate in toluene, reacted for 5 hours at 110° C., made free of solvent, whereby obtaining an [urethane-modified polyester (1)] whose Mw was 72,000 and whose isocyanate content was 0.7%.

On the other hand, 570 parts of bisphenol A EO 2-mole adduct and 217 parts of terephthalic acid were subjected to a polycondensation at 230° C. for 6 hours similarly as described above to obtain a non-modified [polyester (2)] whose Mn was 2,400, whose hydroxyl value was 51 and whose acid value was 5.

200 parts of the [urethane-modified polyester (1)] and 800 parts of the [polyester (2)] were dissolved and mixed in 2000 parts of ethyl acetate to obtain a [resin solution 1].

A part of the [resin solution 1] was dried to isolate a resin portion. The Tg of the resin portion was 55° C.

A beaker was charged with 500 parts of water and 4 parts of nonylphenyl EO 14-mole adduct (Nonipol 200, SANYO KASEI KOGYO), which were dissolved uniformly. A TK homomixer was used to stir the mixture at 18,000 rpm while adding the [resin solution 1] with stirring for 15 minutes. Then this mixture was transferred into a reaction vessel fitted with a stirrer and a thermometer, which was heated to distill ethyl acetate off, and further heated to 98° C. to effect a reaction for 5 hours, whereby obtaining a [resin microparticle (A3) dispersion] consisting of a mixture of a water elongation product of the [urethane-modified polyester (2)] and the [polyester (2)].

The [resin microparticle (A3) dispersion] was observed by an LA-920, which revealed the volume average particle diameter of (A3) was 0.21 μm.

A part of the [resin microparticle (A3) dispersion] was centrifuged and combined with water prior to a further centrifugation which was repeated twice, and then dried to isolate a resin portion {resin microparticle (A3)}. The Tg of (A3) was 64° C.

Production Example 4

A reaction vessel fitted with a stirrer and a thermometer was charged with 787 parts of polycaprolactonediol (Mn: 2,000) and 800 parts of polyether diol (Mn: 4,000, EO content: 50%, PO content: 50%), which were dehydrated under reduced pressure at 120° C. The water content after the dehydration was 0.05%. Then, 55.5 parts of HDI, 65.5 parts of hydrogenated MDI and 0.6 part of dibutyltin dilaurate were added and reacted for 5 hours at 80° C. to obtain a [water-soluble polymer T1].

Then, 100 parts of the [resin microparticle (A1) dispersion], 1 part of the [water-soluble polymer T1] and 107 parts of water were mixed and stirred to obtain a [dispersion 1] as a milky white liquid.

Production Example 5

784 parts of water, 136 parts of the [resin microparticle (A2) dispersion] and 80 parts of a 48.5% aqueous solution of sodium dodecyldiphenyl ether disulfonate [Eleminol MON-7, SANYO KASEI KOGYO] were mixed and stirred to obtain a [dispersion 3] as a milky white liquid.

Production Example 6

634 parts of water, 286 parts of the [resin microparticle (A3) dispersion] and 154 parts of a 48.5% aqueous solution of sodium dodecyldiphenyl ether disulfonate [Eleminol MON-7, SANYO KASEI KOGYO] were mixed and stirred to obtain a [dispersion 3] as a milky white liquid.

Production Example 7

A reaction vessel fitted with a stirrer and a thermometer was charged with 2,000 parts of a polycaprolactone diol whose hydroxyl value was 56 [Placcel L220AL, Daicel Chemical Industries Ltd.] and heated at 110° C. under reduced pressure of 3 mmHg for to effect dehydration for 1 hour. Subsequently, 457 parts of IPDI was added and the reaction was conducted for 10 hours at 110° C. to obtain an urethane polymer [prepolymer 1] having an isocyanate group at the terminal.

The isocyanate content of the [prepolymer 1] was 3.6%.

Production Example 8

A reaction vessel fitted with a condenser, stirrer and nitrogen inlet was charged with 570 parts of bisphenol A EO 2-mole adduct and 217 parts of terephthalic acid, which were subjected to a polycondensation under atmospheric pressure at 230° C. for 6 hours and then under reduced pressure at 230° C. for 6 hours to obtain a non-modified [polyester] whose Mn was 2,600, whose hydroxyl value was 48 and whose acid value was 2, and then subjected to a ring-opening addition of 26 parts of trimellitic anhydride under atmospheric pressure at 180° C. for 2 hours to obtain a [terminal carboxyl group-containing polyester (2)] whose Mn was 2,700, whose hydroxyl value was 35 and whose acid value was 26. 100 parts of this [terminal carboxyl group-containing polyester (2)] was further dissolved in 100 parts of ethyl acetate to obtain a [resin solution 2].

Production Example 9

A reaction vessel fitted with a condenser, stirrer and nitrogen inlet was charged with 160 parts of ethyl acetate, which was heated to 75° C. and then treated dropwise with a mixture of 40 parts of styrene, 120 parts of butyl methacrylate, 60 parts of acrylic acid, 60 parts of ethyl acetate and 0.3 part of azobisisobutyronitrile over a period of 4 hours, and then 0.5 parts of azobisisobutyronitrile was further added and the mixture was matured at 75° C. for 8 hours to obtain a 50%-solid [resin solution (3)] containing a [styrene-acryl copolymer] whose Mn was 4,200, whose hydroxyl value was 0 and whose acid value was 210.

Production Example 10

A reaction vessel fitted with a stirrer and a thermometer was charged with 50 parts of ethylene diamine and 50 parts of MIBK, which were reacted at 50° C. for 5 hours to obtain a ketimine compound [curing agent 1].

Example 1

In a beaker, 150 parts of the [prepolymer 1] and 6 parts of the [curing agent 1] were mixed, combined with 250 parts of the [dispersion 1], and stirred for 1 minute at 9,000 rpm using Ultradisperser (Yamato Scientific Co., Ltd.) at room temperature.

After mixing, the beaker containing the mixture was immersed in a water bath to adjust the temperature of the mixture at 60° C. At this time the viscosity of the mixture was 4,500 mPa·s. The mixture was subjected to shear force for 1 hour at 13,000 rpm in an open-air, and then introduced into a reaction vessel fitted with a stirrer and a thermometer, where the mixture was matured at 50° C. for 8 hours to obtain an aqueous dispersion (X1).

Then, 1 part of an antiblocking agent [Syloid 978, Fuji-Davison Chemical Ltd.] and 0.5 part of a photostabilizer [DIC-TBS, produced by DAINIPPON INK KAGAKU] were added and the mixture was filtered, dried to obtain a composite resin particle (C1). The acid value of a resin particle (B1) obtained as described in EXAMPLE 3 shown below was 0.

Example 2

In a beaker, 150 parts of the [prepolymer 1], 6 parts of the [curing agent 1] and 40 parts of ethyl acetate were mixed, combined with 457 parts of the [dispersion 2], and stirred for 1 minute at 12,000 rpm using a TK homomixer (produced by TOKUSHUKIKA).

After mixing, the beaker containing the mixture was immersed in a water bath to adjust the temperature of the mixture at 60° C. At this time the viscosity of the mixture was 55 mPa·s. The mixture was subjected to shear force for 1 hour at 13,000 rpm in an open-air, and then introduced into a reaction vessel fitted with a stirrer and a thermometer, where the mixture was matured at 50° C. for 8 hours to obtain an aqueous dispersion (X2). Then the mixture was filtered, dried to obtain a composite resin particle (C2). The acid value of a resin particle (B2) was as shown in EXAMPLE 3 described below.

Example 3

100 parts of the aqueous dispersion (X2) was combined with 100 parts of a 5% aqueous solution of sodium hydroxide and mixed using a TK homomixer (TOKUSHUKIKA) at 12,000 rpm for 10 minutes while keeping the temperature at 40° C., whereby dissolving the resin microparticle (A2) depositing on the surface of (C2). Then, the mixture was centrifuged to remove the supernatant, combined with 100 parts of water prior to a further centrifugation which was repeated twice, and then dried to obtain a resin particle (B2). The acid value of (B2) was 0.

Example 4

In a beaker, 150 parts of the [prepolymer 1], 6 parts of the [curing agent 1] and 40 parts of ethyl acetate were mixed, combined with 457 parts of the [dispersion 3], and stirred for 10 minutes at 12,000 rpm using a TK homomixer (TOKUSHUKIKA). After mixing, the beaker containing the mixture was immersed in a water bath to adjust the temperature of the mixture at 80° C. At this time the viscosity of the mixture was 120 mPa·s. The mixture was subjected to shear force for 2 hour at 13,000 rpm in an open-air, and then introduced into a reaction vessel fitted with a stirrer and a thermometer, where the mixture was matured at 50° C. for 8 hours to obtain an aqueous dispersion (X3). Then the mixture was filtered, dried to obtain a composite resin particle (C3). The acid value of a resin particle (B3) obtained as described in EXAMPLE 3 was 0.

Example 5

A beaker was charged with 240 parts of the [resin solution 1], 20 parts of a releasing agent trimethylolpropane tribehenate (melting point: 58° C., melt viscosity: 24 cps) and 4 parts of a colorant copper phthalocyanine, which was stirred for 2 minutes at 12,000 rpm using a TK homomixer at 50° C. to dissolve and disperse uniformly to obtain a [resin solution 1B].

A beaker was charged with 500 parts of an ion exchange water, 500 parts of the [dispersion 1] and 0.2 parts of sodium dodecylbenzene sulfonate, which were dissolved uniformly. Then the mixture was heated to 50° C., stirring at 12,000 rpm using a TK homomixer, while adding 300 parts of the [resin solution 1B] with stirring for 10 minutes.

The beaker containing this mixture was immersed in a water bath to adjust the temperature of the mixture at 60° C.

At this time the viscosity of the mixture was 860 mPa·s. The mixture was subjected to shear force for 2 hour at 13,000 rpm in an open-air, and then the mixture was transferred into a reactor fitted with a stirrer and a thermometer, which was heated to 98° C. to mature the mixture for 5 hours, whereby obtaining an aqueous dispersion (X4). After filtration and drying, a composite resin particle (C4) was obtained. The acid value of a resin particle (B4) obtained as described in EXAMPLE 3 was 4.

Example 6

A beaker was charged with 240 parts of the [resin solution 1], 20 parts of a releasing agent trimethylolpropane tribehenate (melting point: 58° C., melt viscosity: 24 cps) and 4 parts of a colorant copper phthalocyanine, which was stirred for 2 minutes at 12,000 rpm using a TK homomixer at 50° C. to dissolve and disperse uniformly to obtain a [resin solution 1B].

A beaker was charged with 500 parts of the [dispersion 2] which was dissolved uniformly. Then the mixture was heated to 50° C., stirring at 12,000 rpm using a TK homomixer, while adding 214 parts of the [resin solution 1B] with stirring for 10 minutes.

The beaker containing this mixture was immersed in a water bath to adjust the temperature of the mixture at 60° C. At this time the viscosity of the mixture was 64 mPa·s. The mixture was subjected to shear force for 2 hour at 13,000 rpm in an open-air, and then the mixture was transferred into a reactor fitted with a stirrer and a thermometer, which was heated to 98° C. to mature the mixture for 5 hours, whereby obtaining an aqueous dispersion (X5). After filtration and drying, a composite resin particle (C5) was obtained. The acid value of a resin particle (B5) obtained was as shown in EXAMPLE 7 described below.

Example 7

100 parts of the aqueous dispersion (X5) was combined with 100 parts of a 5% aqueous solution of sodium hydroxide and mixed using a TK homomixer (TOKUSHUKIKA) for 10 minutes at 12,000 rpm while keeping the temperature at 40° C., whereby dissolving the resin microparticle (A2) depositing on the surface of (C5). Then, the mixture was centrifuged to remove the supernatant, combined with 100 parts of water prior to a further centrifugation which was repeated twice, and then dried to obtain a resin particle (B5). The acid value of the resin particle (B5) was 4.

Example 8

In a beaker, 75 parts of the [prepolymer 1], 150 parts of the [resin solution 2] and 3 parts of the [curing agent 1] were mixed, combined with 400 parts of the [dispersion 1], and stirred for 1 minute at 9,000 rpm using Ultradisperser (Yamato Scientific Co., Ltd.) at room temperature.

After mixing, the beaker containing the mixture was immersed in a water bath to adjust the temperature of the mixture at 25° C., and then a shear force was given at 13,000 rpm for 10 minutes, and the mixture was introduced into a reaction vessel fitted with a stirrer and a thermometer, and adjusted at 50° C. At this time the viscosity of the mixture was 4,200 mPa·s. Thereafter, the mixture was matured in an open-air at 50 rpm and 50° C. for 8 hours to obtain an aqueous dispersion (X6).

Then, 1 part of an antiblocking agent [Syloid 978, Fuji-Davison Chemical Ltd.] and 0.5 part of a photostabilizer [DIC-TBS, DAINIPPON INK KAGAKU] were added and the mixture was filtered, dried to obtain a composite resin particle (C6). The acid value of a resin particle (B6) obtained as described in EXAMPLE 3 was 12, and the Tg was 60° C.

100 parts of the composite resin particle was combined further with 20 parts of an MEK oxime-blocked HDI and stirred using a Henschel mixer for 30 minutes to effect impregnation, whereby obtaining a paint resin particle (TC6).

Example 9

In a beaker, 30 parts of the [prepolymer 1], 270 parts of the [resin solution 2], 0.6 part of the [curing agent 1] and 40 parts of ethyl acetate were mixed, combined with 700 parts of the [dispersion 2], and stirred for 1 minute at 12,000 rpm using a TK homomixer (TOKUSHUKIKA).

After mixing, the beaker. containing the mixture was immersed in a water bath to adjust.the temperature of the mixture at 25° C., and then a shear force was given at 13,000 rpm for 5 minutes, and the mixture was introduced into a reaction vessel fitted with a stirrer and a thermometer, and adjusted at 50° C. At this time the viscosity of the mixture was 52 mPa·s. Thereafter, the mixture was placed in an open-air and removed the solvents and dehydrated matured at 100 rpm and 50° C. for 8 hours to obtain an aqueous dispersion (X7). Then the mixture was filtered and dried to obtain a composite resin particle (C7). The acid value of the resin particle (B7) was as shown in EXAMPLE 10 described below.

100 parts of the composite resin particle was combined further with 20 parts of an MEK oxime-blocked HDI and stirred using a Henschel mixer for 30 minutes to effect impregnation, whereby obtaining a paint resin particle (TC7).

Example 10

100 parts of the aqueous dispersion (X7) was combined with 100 parts of a 5% aqueous solution of sodium hydroxide and mixed using a TK homomixer (TOKUSHUKIKA) at 12,000 rpm for 10 minutes while keeping the temperature at 40° C., whereby dissolving the resin microparticle (A2) depositing on the surface of (C7) Then, the mixture was centrifuged to remove the supernatant, combined with 100 parts of water prior to a further centrifugation which was repeated twice, and then dried to obtain a resin particle (B7). The acid value of the resin particle (B7) was 21, and the Tg was 58° C.

100 parts of the resin particle was combined further with 20 parts of an MEK oxime-blocked HDI and stirred using a Henschel mixer for 30 minutes to effect impregnation, whereby obtaining a paint resin particle (TB7).

Example 11

In a beaker, 200 parts of the [prepolymer 1], 200 parts of the [resin solution 2], 4 parts of the [curing agent 1] and 40 parts of ethyl acetate were mixed, combined with 620 parts of the [dispersion 3], and stirred for 10 minutes at 12,000 rpm using a TK homomixer (TOKUSHUKIKA). After mixing, the beaker containing the mixture was immersed in a water bath to adjust the temperature of the mixture at 60° C. At this time the viscosity of the mixture was 140 mPa·s. The mixture was subjected to shear force at 60° C. for 2 hours at 13,000 rpm in an open-air, and then the mixture was transferred into a reactor fitted with a stirrer and a thermometer, which was heated to 50° C. to mature the mixture for 8 hours, whereby obtaining an aqueous dispersion (X8). After filtration and drying, a composite resin particle (C8) was obtained. The acid value of a resin particle (B8) obtained as described in EXAMPLE 3 was 9 and the Tg was 62° C.

100 parts of the composite resin particle was combined further with 20 parts of an MEK oxime-blocked HDI and stirred using a Henschel mixer for 30 minutes to effect impregnation, whereby obtaining a paint resin particle (TC8).

Example 12

A beaker was charged with 40 parts of the [prepolymer 1], 400 parts of the [resin solution 2], 0.8 part of the [curing agent 1], 20 parts of a releasing agent trimethylolpropane tribehenate (melting point: 58° C., melt viscosity: 24 cps) and 4 parts of a colorant copper phthalocyanine, which was stirred for 2 minutes at 12,000 rpm using a TK homomixer at 50° C. to dissolve and disperse uniformly to obtain a [resin solution 2B1].

A beaker was charged with 500 parts of an ion exchange water, 500 parts of the [dispersion 1] and 0.2 part of sodium dodecylbenzene sulfonate, which were dissolved uniformly. Then the mixture was heated to 25° C., stirring at 12,000 rpm using a TK homomixer, while adding 300 parts of the [resin solution 2B1] with stirring for 10 minutes.

The beaker containing this mixture was immersed in a water bath to adjust the temperature of the mixture at 60° C., and then a shear force was given for 2 hour at 10,000 rpm, and then the mixture was transferred into a reactor fitted with a stirrer and a thermometer, which was heated to 98° C. At this time the viscosity of the mixture was 880 mpa·s. The mixture was reacted at 500 rpm and 98° C. for 5 hours, whereby obtaining an aqueous dispersion (X9). After filtration and drying, a composite resin particle (C9) was obtained. The acid value of a resin particle (B9) obtained as described in EXAMPLE 3 was 24, and the Tg was 57° C.

100 parts of the composite resin particle was combined further with 20 parts of an MEK oxime-blocked HDI and stirred using a Henschel mixer for 30 minutes to effect impregnation, whereby obtaining a paint resin particle (TC9).

Example 13

A beaker was charged with 240 parts of the [resin solution 2], 20 parts of a releasing agent trimethylolpropane tribehenate (melting point: 58° C., melt viscosity: 24 cps) and 4 parts of a colorant copper phthalocyanine, which was stirred for 2 minutes at 12,000 rpm using a TK homomixer at 50° C. to dissolve and disperse uniformly to obtain a [resin solution 2B2].

A beaker was charged with 500 parts of the [dispersion 2] which was dissolved uniformly. Then the mixture was heated to 50° C., stirring at 12,000 rpm using a TK homomixer, while adding 214 parts of the [resin solution 2B2] with stirring for 10 minutes.

The beaker containing this mixture was immersed in a water bath to adjust the temperature of the mixture at 60° C. At this time the viscosity of the mixture was 84 mPa·s. The mixture was subjected to shear force at 60° C. for 2 hour at 13,000 rpm in an open-air, and then the mixture was transferred into a reactor fitted with a stirrer and a thermometer, which was heated with stirring at 100 rpm to 98° C. to react for 5 hours, whereby obtaining an aqueous dispersion (X10). After filtration and drying, a composite resin particle (C10) was obtained. The acid value of a resin particle (B10) obtained was as shown in EXAMPLE 14 described below.

100 parts of the composite resin particle was combined further with 20 parts of an MEK oxime-blocked HDI and stirred using a Henschel mixer for 30 minutes to effect impregnation, whereby obtaining a paint resin particle (TC10).

Example 14

100 parts of the aqueous dispersion (X10) was combined with 100 parts of a 5% aqueous solution of sodium hydroxide and mixed using a TK homomixer (TOKUSHUKIKA) at 12,000 rpm for 10 minutes while keeping the temperature at 40° C., whereby dissolving the resin microparticle (A2) depositing on the surface of (C10). Then, the mixture was centrifuged to remove the supernatant, combined with 100 parts of water prior to a further centrifugation which was repeated twice, and then dried to obtain a resin particle (B10). The acid value of the resin particle (B10) was 22, and the Tg was 59° C.

100 parts of the resin particle was combined further with 20 parts of an MEK oxime-blocked HDI and stirred using a Henschel mixer for 30 minutes to effect impregnation, whereby obtaining a paint resin particle (TB4).

Comparative Example 1

In a beaker, 150 parts of the [prepolymer 1] and 6 parts of the [curing agent 1] were mixed, combined with 250 parts of the [dispersion 1]; and stirred at room temperature using Ultradisperser (produced by Yamato Scientific Co., Ltd.) at 9,000 rpm for 1 minute.

After mixing, the mixture was introduced to a reaction vessel fitted with a stirrer and a thermometer, and adjusted at 50° C. At this time, the viscosity of the mixture was 5,200 mPa·s. Thereafter, the reaction was conducted at 100 rpm at 50° C. for 10 hours to obtain an aqueous dispersion (HX1).

Then, 1 part of an antiblocking agent [Syloid 978, produced by Fuji-Davison Chemical Ltd.] and 0.5 part of a photostabilizer [DIC-TBS, produced by DAINIPPON INK KAGAKU] were added and the mixture was filtered, dried to obtain a composite resin particle (HC1). The acid value of a resin particle (HB1) was 0, and the Tg was 57° C.

100 parts of the composite resin particle was combined further with 20 parts of an MEK oxime-blocked HDI and stirred using a Henschel mixer for 30 minutes to effect impregnation, whereby obtaining a paint resin particle (THC1).

Comparative Example 2

In a beaker, 150 parts of the [prepolymer 1], 6 parts of the [curing agent 1] and 40 parts of ethyl acetate were mixed, combined with 457 parts of the [dispersion 2], and stirred for 10 minute at 12,000 rpm using a TK homomixer (produced by TOKUSHUKIKA).

After mixing, the mixture was introduced to a reaction vessel fitted with a stirrer and a thermometer, and adjusted at 50° C. At this time, the viscosity of the mixture was 120 mPa·s. Thereafter, the reaction and removal of the solvents was conducted at 50 rpm at 50° C. for 10 hours to obtain an aqueous dispersion (HX2). After filtration and drying, a composite particle resin (HC2) was obtained. The acid value of the resin particle (HB2) was 0.

Comparative Example 3

In a beaker, 450 parts of the [resin solution (3)], 50 parts of the [prepolymer 1] and 1 part of the [curing agent 1] were mixed, combined with 1,000 parts of the [dispersion 2], and stirred for 10 minutes at 12,000 rpm using a TK homomixer (TOKUSHU KIKA KOGYO CO., LTD.).

After mixing, the mixture was introduced to a reaction vessel fitted with a stirrer and a thermometer, made free of the solvent and reacted at 50° C. for 10 hours to obtain an aqueous dispersion (HX3). After filtration and drying, a composite particle resin (HC3) was obtained. The acid value of the resin particle (HB3) was 180 and the Tg was 94° C.

100 parts of the composite resin particle was combined further with 20 parts of an MEK oxime-blocked HDI and stirred using a Henschel mixer for 30 minutes to effect impregnation, whereby obtaining a paint resin particle (THC3).

<Determination of Physical Parameters>

Particles (C1) to (C10), (B2), (B5), (B7), (B10), (HC1) to (HC3) obtained in EXAMPLES 1 to 14 and COMPARATIVE EXAMPLES 1 to 3 were dispersed in water and measured the particle size distribution by a Coulter counter.

The (TA/TC), variation coefficient, BET specific surface area, surface average center line toughness and shape factor (SF-1, SF-2) of each of the composite resin particles and resin particles were measured by the methods described above.

An angle of repose was measured using a powder tester PT-R (produced by HOSOKAWA MICRON CORPORATION).

The viscosity of a dispersion was evaluated by measuring the viscosity (Brookfield viscometer, 25° C.) of a dispersion obtained by dispersing 55 parts of a composite resin particle or a resin particle uniformly with stirring in a solution of 2 parts of a 48.5% aqueous solution of sodium dodecyldiphenyl ether disulfonate [Eleminol MON-7, produced by SANYO KASEI KOGYO] in 45 parts of a 7/3 mixture of water/isopropyl alcohol (weight basis).

Furthermore, each particle was examined for the anti-heat storage stability by investigating whether the melt adhesion occurred or not after storage for 7 days at 40° C. In this investigation, 50 g of each stored resin particle was shaken on a 150 μm mesh size sieve for 15 minutes, and the amount of the resin particle remaining on the sieve was measured and its rate was judged by the criteria shown below.

◎: Aggregation less than 0.2%.

○: Aggregation less than 1.0%.

Δ: Aggregation less than 2.0%.

x: Aggregation of 2.0% or more

Moreover, each of the above-mentioned paint resin particles (TC6) to (TC10), (B7), (B10), (HC1) and (HC3) was coated electrostatically to a thickness of 40 to 60 μm using a commercial corona charge spray gun onto a zinc phosphate-treated steel standard plate produced by NIPPON TEST PANEL, baked at 180° C. for 20 minutes, and then subjected to a shear adhesion test in accordance with the method prescribed in JIS K6830. The adhesion (adhesiveness) was evaluated on the basis of the criteria shown below.

○: Complete cohesion failure

Δ: Vestiginal destruction with partial interfacial failure x: Complete interfacial failure A paint resin particle was coated and baked similarly to the procedure described above and then immersed in a warm water at 40° C. for 10 days. Then, the shear adhesion test was conducted in accordance with the method prescribed in JIS K6830. The water resistant adhesiveness property was evaluated on the basis of the criteria similar to that for the adhesion (adhesiveness) described above.

EXAMPLES and COMPARATIVE EXAMPLES according to the first aspect of the invention are shown in Table 1, while EXAMPLES and COMPARATIVE EXAMPLES according to the second aspect of the invention are shown in Table 2. A part of EXAMPLES in Table 2 serve to EXAMPLES according to the first aspect.

TABLE 1

| | EXAMPLE | | | | | | | COMPARATIVE EXAMPLE | |
| --- | --- | --- | --- | --- | --- | --- | --- | --- | --- |
| | 1 | 2 | 3 | 4 | 5 | 6 | 7 | 1 | 2 |
| Composite resin particle or resin particle | C1 | C2 | B2 | C3 | C4 | C5 | B5 | HC1 | HC2 |
| Shape factor SF-1 | 162 | 183 | 184 | 350 | 163 | 171 | 168 | 105 | 108 |
| Shape factor SF-2 | 210 | 240 | 235 | 180 | 215 | 222 | 231 | 221 | 243 |
| Resin particle (A) content wt % | 16.3 | 10.7 | ≦0.1 | 10.7 | 33.5 | 19.1 | ≦0.1 | 16.0 | 10.1 |
| Volume average particle diameter μm of resin particle (A) | 0.80 | 0.12 | — | 0.21 | 0.80 | 0.12 | — | 0.80 | 0.12 |
| Volume average particle diameter μm | 133 | 7.2 | 7.1 | 7.5 | 4.1 | 5.2 | 4.8 | 131 | 7.1 |

TABLE 1-continued

|  | EXAMPLE | | | | | | | COMPARATIVE EXAMPLE | |
|---|---|---|---|---|---|---|---|---|---|
|  | 1 | 2 | 3 | 4 | 5 | 6 | 7 | 1 | 2 |
| (Volume average particle diameter)/(number average particle diameter) | 1.12 | 1.11 | 1.12 | 1.15 | 1.09 | 1.10 | 1.08 | 1.12 | 1.11 |
| Variation coefficient of volume average particle diameter | 10.2 | 12.0 | 9.8 | 12.6 | 7.3 | 8.1 | 6.6 | 10.1 | 12.1 |
| TA/TC | 0.96 | 0.91 | ≦0.01 | 0.80 | 0.95 | 0.89 | ≦0.01 | 0.98 | 0.96 |
| BET specific surface area $m^2/g$ | 2.1 | 3.9 | 4.4 | 4.0 | 3.6 | 5.7 | 5.9 | 2.0 | 3.8 |
| Surface average center line roughness μm | 0.59 | 0.18 | 0.23 | 0.25 | 0.51 | 0.33 | 0.18 | 0.61 | 0.21 |
| Angle of repose | 43 | 46 | 54 | 52 | 55 | 52 | 56 | 33 | 36 |
| Resinparticle dispersion viscosity | 45 | 123 | 144 | 166 | 254 | 181 | 283 | 28 | 62 |
| Anti-heat storage stability | ⊚ | ⊚ | ○ | ○ | ⊚ | ⊚ | ○ | ○ | ⊚ |

TABLE 2

|  | EXAMPLE | | | | | | | COMPARATIVE EXAMPLE | |
|---|---|---|---|---|---|---|---|---|---|
|  | 8 | 9 | 10 | 11 | 12 | 13 | 14 | 1 | 3 |
| Composite resin particle or resin particle | C6 | C7 | B7 | C8 | C9 | C10 | B10 | HC1 | HC3 |
| Volume average particle diameter μm | 125 | 8.3 | 9.2 | 6.3 | 5.5 | 8.2 | 5.9 | 131 | 6.3 |
| (Volume average particle diameter)/(number average particle diameter) | 1.12 | 1.11 | 1.12 | 1.15 | 1.09 | 1.10 | 1.15 | 1.12 | 1.11 |
| Resin particle (A) content (wt %) | 16.8 | 9.4 | ≦1 | 8.8 | 31.4 | 23.6 | ≦1 | 16.0 | 11.2 |
| Volume average particle diameter μm of resin particle (A) | 0.80 | 0.12 | — | 0.21 | 0.80 | 0.12 | — | 0.80 | 0.12 |
| Variation coefficient of volume average particle diameter | 10.2 | 12.3 | 8.9 | 11.8 | 7.1 | 8.5 | 6.3 | 10.1 | 12.4 |
| TA/TC | 0.95 | 0.90 | ≦0.1 | 0.81 | 0.93 | 0.88 | ≦1 | 0.98 | 0.93 |
| BET specific surface area $m^2/g$ | 1.1 | 4.81 | 4.1 | 6.2 | 8.5 | 4.4 | 7.8 | 2.0 | 8.3 |
| Surface average center line roughness μm | 0.58 | 0.17 | 0.21 | 0.24 | 0.44 | 0.31 | 0.12 | 0.61 | 0.22 |
| Shape factor SF-1 | 105 | 106 | 110 | 185 | 187 | 210 | 174 | 105 | 111 |
| Shape factor SF-2 | 213 | 245 | 241 | 206 | 261 | 255 | 247 | 221 | 241 |
| Angle of repose | 34 | 39 | 41 | 52 | 54 | 56 | 51 | 33 | 37 |
| Resinparticle dispersion viscosity | 34 | 68 | 71 | 152 | 184 | 189 | 211 | 28 | 71 |
| Anti-heat storage stability | ⊚ | ⊚ | ○ | ⊚ | ⊚ | ⊚ | ⊚ | ○ | X |
| adhesiveness | ○ | ○ | ○ | ○ | ○ | ○ | ○ | Δ | X |
| Water resistant adhesiveness property | ○ | ○ | ○ | Δ | ○ | ○ | ○ | X | X |

Based on the results shown in Table 1, each composite resin particle according to the first aspect of the present invention revealed to be excellent in terms of the powder flawability and the viscosity profile of a dispersion made therefrom when compared with an analogous composition of COMPARATIVE EXAMPLES and also to have an equivalent or rather improved anti-heat storage stability. Furthermore, the results shown in Table 2 also indicate that each composite resin particle according to the second aspect of the invention revealed to be excellent in terms of the anti-heat storage stability, the adhesiveness property and the water resistant adhesiveness property, and EXAMPLES 11 to 13 which are also the composite resin particles of the first aspect are excellent also in terms of the powder flawability and the viscosity profile of a dispersion.

INDUSTRIAL APPLICABILITY

A composite resin particle according to the first aspect of the present invention has a uniform particle diameter, and excellent powder flawability and storage stability. In addition, it exhibits a marked thixotropy upon dispersing in a solvent or in an aqueous solvent. Accordingly it is useful as a fluidity improving agent for a paint or a coating.

In addition, it is aligned in the longitudinal direction of the resin particle upon forming a coating film. Accordingly, an advantage such as a suppression of swelling or a promotion of luster or gloss can be experienced.

It also allows a smooth touch to be experienced upon application to a skin when incorporated into a cosmetic product such as a lipstick, foundation and the like.

It also gives an improved cleaning performance at a cleaning blade when used as a toner.

A composite resin particle according to the second aspect of the present invention exhibits an extremely excellent adhesion (adhesiveness) with a substrate. It has a high affinity especially to a substrate of metal, paper and wood, and exhibits a high adhesiveness to such an article.

Accordingly, when used as a paint additive, it gives a coating film which exhibits an extremely high adhesion (adhesiveness) with a substrate, resulting in a difficulty in peeling the paint off.

Also when used as a toner, it gives an extremely high adhesion (adhesiveness with a paper, resulting in a difficulty in undergoing an offset even when fixed at a low temperature.

What is claimed is:

1. A composite resin particle comprising a resin microparticle (A) depositing on the surface of a resin particle (B) wherein the shape factor (SF-1) of said composite resin particle is 145 to 800.

2. The composite resin particle of claim 1, wherein the acid value of a resin (b) constituting the resin particle (B) is 7 to 100.

3. The composite resin particle according to claim 2 wherein the resin microparticle (A) has a volume average particle diameter (DA) of 0.0005 to 30 μm and the resin particle (B) has a volume average particle diameter (DB) of 0.1 to 300 μm.

4. The composite resin particle according to claim 2 wherein the resin microparticle (A) and/or the resin particle (B) is at least one resin selected from the group consisting of polyurethane, epoxy resin, vinyl resin and polyester.

5. The composite resin particle according to claim 2 wherein the resin particle comprises a reactive group-containing prepolymer (α) and a curing agent (β).

6. The composite resin particle according to claim 2 obtained in such a manner that the resin (b) constituting the resin particle (B), a precursor (b0) of said resin (b) and/or a solution thereof are dispersed in an aqueous dispersion containing the resin microparticle (A) and if the precursor (b0) or a solution thereof is employed the precursor (b0) is reacted, to form the resin particle (B) comprising said resin (b) in the aqueous dispersion of the resin microparticle (A) whereby forming the resin particle as the resin particle (B) on the surface of which the resin microparticle (A) has been deposited and then the aqueous solvent is removed.

7. The composite resin particle according to claim 1 wherein the resin microparticle (A) has a volume average particle diameter (DA) of 0.0005 to 30 μm and the resin particle (B) has a volume average particle diameter (DB) of 0.1 to 300 μm.

8. The composite resin particle according to claim 1 wherein the ratio (DA/DB) of the volume average particle diameter (DA) of the resin microparticle (A) to the volume average particle diameter (DB) of the resin particle (B) is 0.0001 to 0.5.

9. The composite resin particle according to claim 1 wherein the amount of the resin microparticle (A) based on the total weight of the resin microparticle (A) and the resin particle (B) is 0.01 to 60% by weight.

10. The composite resin particle according to claim 1 wherein the ratio (TA/TC) of the projected area (TA) of the resin microparticle (A) to the projected area (TC) of the composite resin particle is 0.001 to 1.

11. The composite resin particle according to claim 1 wherein the variation coefficient of the volume average particle diameter (DC) of the composite resin particle is 0.1 to 50%.

12. The composite resin particle according to claim 1 wherein the ratio (DC/DNC) of the volume average particle diameter (DC) of the composite resin particle to the number average particle diameter (DNC) of the composite resin is 1.0 to 2.5.

13. The composite resin particle according to claim 1 wherein the resin microparticle (A) and/or the resin particle (B) is at least one resin selected from the group consisting of polyurethane, epoxy resin, vinyl resin and polyester.

14. The composite resin particle according to claim 1 wherein the resin particle (B) contains a colorant treated with an aluminum coupling agent.

15. The composite resin particle according to claim 1 wherein the Tg of the resin microparticle (A) is 0 to 300° C.

16. The composite resin particle according to claim 1 wherein the resin particle comprises a reactive group-containing prepolymer (α) and a curing agent (β).

17. The composite resin particle according to claim 16 wherein the reactive group-containing prepolymer (α) contains at least one reactive group selected from the group consisting of isocyanate group, blocked isocyanate group and epoxy group and also wherein the curing agent (β) is an active hydrogen-containing compound (β1) which may be blocked with a compound which can be removed.

18. The composite resin particle according to claim 17 wherein the active hydrogen-containing compound (β1) is a ketimine and/or water.

19. The composite resin particle according to claim 1 obtained in such a manner that the resin (b) constituting the resin particle (B), a precursor (b0) of said resin (b) and/or a solution thereof are dispersed in an aqueous dispersion containing the resin microparticle (A) and if the precursor (b0) or a solution thereof is employed the precursor (b0) is reacted, to form the resin particle (B) comprising said resin (b) in the aqueous dispersion of the resin microparticle (A) whereby forming the resin particle as the resin particle (B) on the surface of which the resin microparticle (A) has been deposited and then the aqueous solvent is removed.

20. The composite resin particle according to claim 19 obtained in such a manner that the aqueous dispersion is subjected to a high shear force upon dispersing if said resin (b) and/or the precursor (b0) is employed, and upon dispersing and if necessary upon removing the solvent if a solution of said resin (b) and/or a solution of the precursor (b0) is employed.

* * * * *